United States Patent
Wolter et al.

(10) Patent No.: US 10,259,829 B2
(45) Date of Patent: Apr. 16, 2019

(54) BIODEGRADABLE HYBRID POLYMERS USABLE IN MEDICAL TECHNOLOGY OR IN BIOLOGY, STARTING SILANES THEREFOR, AND PREPARATION PROCESS THEREFOR AND USES THEREOF

(71) Applicant: Fraunhofer-Gesellschaft Zur Forderung der Angewandten Forschung E.V., Munich (DE)

(72) Inventors: Herbert Wolter, Tauberbischofsheim (DE); Somchith Nique, Eisingen (DE); Kerstin Obel, Tubingen (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/509,373

(22) PCT Filed: Aug. 28, 2015

(86) PCT No.: PCT/EP2015/069775
§ 371 (c)(1),
(2) Date: Mar. 7, 2017

(87) PCT Pub. No.: WO2016/037871
PCT Pub. Date: Mar. 17, 2016

(65) Prior Publication Data
US 2017/0313726 A1    Nov. 2, 2017

(30) Foreign Application Priority Data

Sep. 8, 2014 (DE) .......... 10 2014 112 907
Dec. 17, 2014 (DE) .......... 10 2014 118 901
Jul. 7, 2015 (DE) .......... 10 2015 110 979

(51) Int. Cl.
C07F 7/04    (2006.01)
C07F 7/08    (2006.01)
C08G 77/02   (2006.01)
C08G 77/20   (2006.01)
C08G 77/00   (2006.01)

(52) U.S. Cl.
CPC ............ C07F 7/045 (2013.01); C07F 7/0834 (2013.01); C08G 77/02 (2013.01); C08G 77/20 (2013.01); C08G 77/70 (2013.01)

(58) Field of Classification Search
None
See application file for complete search history.

(56) References Cited

U.S. PATENT DOCUMENTS 9,539,763 B2 *    1/2017    Houbertz-Krauss ..... C07H 9/04

FOREIGN PATENT DOCUMENTS

| JP | 08199036 A * | 8/1996 | |
| JP | H08 199036 | 8/1996 | |
| WO | 86/000084 | 1/1986 | |
| WO | WO 8600084 A1 * | 1/1986 | ......... B29C 44/3446 |
| WO | 2011/098460 | 8/2011 | |

OTHER PUBLICATIONS

ISA Written Opinion (IPEA Report on Patentability Int'l Applic. PCT/EP2015/069775).*
International Preliminary Report on Patentability dated Aug. 24, 2016 for International Patent Application No. PCT/EP2015/069775 [English Translation].
Christenson et al. J Biomed Mater Res (2004) 70A: 245-255.
Claeyssens et al. Langmuir (2009) 25(5): 3219-3223.
Doraiswamy et al. Mater. Res. Soc. Symp. Proc. (2005) 845: AA2.4.1-AA2.4.6.
Doraiswamy et al. Acta Biomaterialia (2006) 2: 267-275.
Houbertz, Ruth, Steenhusen, Sönke, Stiche, Thomas1, and Sext, Gerhard (2010). Two-Photon Polymerization of Inorganic-Organic Hybrid Polymers as Scalable Technology Using Ultra-Short Laser Pulses, Coherence and Ultrashort Pulse Laser Emission, Dr. F. J. Duarte (Ed.).
Ishizone et al. Macromolecules (2003) 36: 42-49.
Kristensen et al. Org Lett. (2009) 11(14)-2971.
Liu et al. Marcomol. Chem. Phys. (2004) 205: 2205-2213.
Tian et al. Journal of Polymer Science (1997) 2295-2309.

* cited by examiner

Primary Examiner — Clinton A Brooks
Assistant Examiner — Kofi Adzamli
(74) Attorney, Agent, or Firm — Hunton Andrews Kurth LLP

(57) ABSTRACT

The invention relates to a silane or silane mixture obtainable by reacting a hydrolysable silane of the formula (A): SiR4 in which R is a hydrolytically condensable group or hydroxyl with a compound R*(OH)x where x is 1, 2, 3 or greater 3, where R* has a straight-chain or branched hydrocarbon skeleton which, according to the number x, is monovalent, divalent, trivalent or multivalent, and has a hydrocarbonaceous chain interrupted by at least two —C(O)O— groups, wherein there are a maximum of 8 successive carbon atoms in the individual hydrocarbon units formed by interruptions within this chain and the, or in the case of branched structures at least one, end of the hydrocarbonaceous chain at the opposite end to the sole hydroxyl group or one of the hydroxyl groups bears an organically polymerizable group, wherein the alcohol is otherwise unsubstituted or has further substituents. The invention further relates to an organically modified silica polycondensate formed as a result of hydrolytic condensation of the silane or silane mixture and optionally a subsequent organic polymerization of the organically polymerizable groups, with optional addition of an organic, at least difunctional compound to the silica polycondensate prior to the organic polymerization.

13 Claims, 3 Drawing Sheets

BIODEGRADABLE HYBRID POLYMERS USABLE IN MEDICAL TECHNOLOGY OR IN BIOLOGY, STARTING SILANES THEREFOR, AND PREPARATION PROCESS THEREFOR AND USES THEREOF

CROSS-REFERENCE TO RELATED APPLICATIONS

This application is a national-stage filing of International Patent Application PCT/EP2015/069775, filed Aug. 28, 2015, which claims priority German Patent Application DE 10 2015 110 979.4, filed Jul. 7, 2015, German Patent Application DE 10 2014 118 901.9, filed Dec. 17, 2014, and German Patent Application DE 10 2014 112 907.5, filed Sep. 8, 2014, the disclosure of each of which are hereby incorporated by reference.

The present invention relates to new, inorganically condensable silanes and condensates and/or polymers thereof. These silanes contain one or more substituents(s) or groups having ester bonds and, where applicable additionally ether bonds and/or thioether bonds, linked via oxygen to the silicon groups, as well as organic polymerizable units such as C=C double bonds or ring-opening systems, for example epoxy groups. The silanes can be condensed inorganically or polymerized organically via the C=C double bonds. Such an organic polymerization can for example be carried out with the aid of 2-photon polymerization (2PP) to obtain structured, essentially monomer-free materials. These are stable with respect to irradiation with γ-rays and can therefore be sterilized. By varying the content of inorganic cross-linkable units and/or organic polymerizable units, the mechanical properties of hybrid polymers produced from the silanes can be adjusted to resemble those of natural hard or soft tissue. They can be populated by cell types such as endothelian cells and are thus suitable for example as scaffolds for the stabilization and growth of cells. The hybrid polymers are more or less degraded within a few weeks when stored in buffers, generating toxically nonhazardous, frequently water-soluble, small degradation products such as $C_2$-dicarboxylic acids. Further, the oxygen bridge between the ester group-containing substituent and the silicon atom is cleaved. This makes the hybrid polymers of the present invention suitable for the production of biodegradable or absorbable implants and scaffolds having mechanical properties adapted to the respective use.

The restoration of diseased or damaged tissue remains one of the biggest challenges of regenerative medicine. The growth of cells on three-dimensional (3D), mostly porous "scaffolds" (finely structured frameworks) to form tissues ("tissue engineering", briefly T.E.) is a promising approach for the production of autologous tissue. Scaffolds for T.E. have to be biocompatible and biodegradable, they should promote cell adhesion and cell proliferation and should be adapted to the mechanical requirements of the respective tissue.

A number of processes exist for the production of scaffolds. The most frequent established methods are solvent-casting, particulate leaching, gas foaming, phase separation, freeze-drying, electro-spinning und self-assembly. However, none of these production methods allows a precise control of pore size, pore geometry and spatial distribution of the pores. Moreover, an interconnectivity cannot be ensured. More recent processes avoid these disadvantages. For the production of high-complex structures, three-dimensional objects can be assembled from several layers with the aid of a computer-generated design (computer-aided designs, CAD). Processes utilizing this technique are known as rapid prototyping processes or solid-free-form processes. With these methods, anatomically adapted scaffolds can be generated based on computer tomography (CT) data or magnetic resonance tomography (MRT) data. Stereolithography is frequently used. In this technique, a chemical reaction—photopolymerization—is initiated by electromagnetic radiation. The material to be structured or the material composition to be structured therefore has to be capable of reacting with light. Thereby, a phase transfer from liquid to solid takes place in exposed areas. In a subsequent developing step, only the remaining liquid material is dissolved. In this manner, structures can be formed layer-wise with the aid of a laser beam. This method is advantageous in that highly organized three-dimensional scaffolds having a defined porosity, pore size and interconnectivity of the pores can be produced with high reproducibility and that this is possible with only few process steps. However, limitations in the choice of polymers and upscaling problems are disadvantageous. A specific type of stereolithography, namely two photon polymerization (2PP), provides a good resolution. This technique allows the generation of ultrafine structures at high resolution. The method is based on the simultaneous absorption of two photons (two photon absorption, TPA), which triggers the decomposition of the initiator molecules and thereby also the subsequent chemical reaction between the produced radicals and the monomers. Due to the simultaneous absorption of two photons, very high light intensities are required for the stimulation which can be realized by ultrashort laser pulses. The rate of the two photon absorption depends on the intensity nonlinearly. Thus, the polymerization takes place only in a spatially restricted area around the laser focal point, whereby even resolutions of <100 nm can be achieved. If the focal point is made to move through the material, three-dimensional microstructures are produced in the exposed areas in one process step. This method is advantageous in that the shape of the scaffold and also the intrinsic porosity of the structure can be controlled. The physiological effect of extracellular matrix (ECM) is to provide a possibility for cells in the body to adhere and to control cell functions and tissue functions such as differentiation, growth, reproduction and interactions between cells.

To adequately mimic the ECM for tissue engineering, scaffolds made of biopolymers produced by 2PP are well suitable from a chemical point of view. If degradable scaffold materials are used, it is possible to provide space for cell migration and cell expansion under physiological conditions due to the decomposition of the scaffold/network structure.

In the medical technology, for a long time suitable materials have been searched which can be structured in a targeted manner and which are biodegradable even though organic groups, in particular (meth)acrylate and other C=C double bonds, have been polymerized. For example, F. Claeyssens et al. in "Three-Dimensional Biodegradable Structures Fabricated by Two-Photon-Polymerization", Langmuir 25, 3219-3223 (2009) have shown that structures which might be used as a scaffold can be produced from the biodegradable three block copolymer poly (ε-caprolactone-co-trimethylenecarbonate)-b-poly(ethyleneglycol)-b-poly (ε-caprolactone-co-trimethylenecarbonate) with a photoinitiator using two photon polymerization. Biodegradable organic polymerizable hybrid polymers have also been considered to this end. These are normally modifications of known ORMOCER®s, i.e. hydrolytically condensed silane compounds carrying organically cross-linkable groups. Some of these ORMOCERs have already been described as being inherently biocompatible, see R. Narayan et al., in

*Mater. Res. Soc. Symp. P* 2005, 845, 51 and in *Acta Biomater.* 2006, 2, 267. Hybrid materials which are at least partially biodegradable under physiological conditions have been described in D. Tian et al. in Journal of Polymer Science, Part A—Polymer Chemistry, "Biodegradable and Biocompatible Inorganic-Organic Hybrid Materials. I. Synthesis and Characterization", 1997, 35(11) 2295-2309. R. Houbertz et al. have shown in *Coherence and Ultrashort Pulse Laser Emission,* 2010, 583 and in WO 2011/098460 A1 biocompatible materials which can be structured by 2PP. These contain either residues linked via Si—C bonds carrying organic polymerizable groups, or they are produced from a mixture of silanes having Si—C linked organic polymerizable residues and organic polymerizable compounds. Examples in WO 2011/098460 A1 showed that such structured materials suffer from a weight loss in buffers such as PBS, which means that they should be biodegradable by hydrolysis to some extent, and can be populated by cells.

Biodegradable purely organic materials produced by polymerization of C=C double bonds are disadvantageous in that they can contain only a relatively low content of organically polymerizable groups in order to ensure biodegradability, which is mainly based on the cleavage of preferably multiple ester groups and/or ether groups. Biodegradable, purely organic materials produced by esterification or the like (thermoplastics), such as polylactides, do not show this disadvantage; however, they cannot be structured by the polymerization and therefore have to formed to their final shape by forming processes. The known ORMOCER® hybrid materials allow solidification through organic polymerization of C=C double bonds and also through inorganic cross-linking reactions (formation of Si—O—Si bridges), wherein the presence of organic polymerizable C=C double bonds allows a spatial structuring in the polymerization. However, the Si—C bonds contained therein are not susceptible to hydrolysis under physiological conditions.

The present inventors have tried to solve the problem to overcome the disadvantages of the prior art and to provide materials which can be more densely cross-linked than purely organic materials and can thereby achieve mechanical properties which could not be adjusted to date, but are on the other hand much better (quicker and/or to larger extent) degradable under physiological conditions than known hybrid materials. Moreover, the materials of the present invention should be sterilizable and biodegradable in order to be suitable for the production of implants and scaffolds.

The object is solved by providing silanes (and also silane blends) and/or silicic acid polycondensates, obtainable by reacting at least one hydrolysable silane represented by the formula (A)

$$SiR_4 \quad (A)$$

wherein R is a hydrolytically condensable group and is preferably selected from among groups having the formula R'COO⁻, or can instead be OR' or OH, wherein R' is a straight-chain or a branched alkyl or an alkyl comprising a non-aromatic ring, and preferably is methyl or ethyl, with at least one monovalent or multivalent compound $R^*(OH)_x$ wherein x is 1, 2, 3 or larger than 3, which is normally composed only of organic components and has a straight-chain or branched hydrocarbon skeleton R*, preferably not containing a ring, which, depending on the number of OH groups, is monovalent, divalent, trivalent or multivalent, and has a hydrocarbon-containing chain of variable length, wherein the carbon atoms can be interrupted by at least two, preferably at least three —C(O)O— groups (ester groups, directed in an arbitrary direction), and—in case silicic acid polycondensates should be provided—optionally a subsequent hydrolytic condensation reaction.

In the hydrocarbon skeleton of R*, in the individual hydrocarbon units formed by interruptions, the number of carbon atoms succeeding each other is 8 or less in the present invention, preferably not more than 6 and more preferably not more than 4 carbon atoms, wherein the chain can again be interrupted by oxygen atoms and/or sulfur atoms, as explained further below. Furthermore, the terminal of the hydrocarbon-containing chain at the opposite/remote end of the hydroxyl group, or in case of branched structures, at least one terminal at the opposite/remote end of the only hydroxyl group or of one of the hydroxyl groups, comprises an organically polymerizable group which is normally selected from groups containing an organically polymerizable C=C double bond which is preferably part of an acrylic group or even more preferably of a methacrylic group, in particular an acrylate group, or more preferably a methacrylate group; and ring-opening systems such as epoxides. The organic polymerization which these groups are capable of can be, but does not have to be, a polyaddition; and can be photochemically, thermally or chemically (2 component polymerization, anaerobic polymerization, redox-induced polymerization) inducible. A combination of self-curing and, for example, photo-induced or thermal curing is also possible. It is noted that the —C(O)O— group of acrylate groups or methacrylate groups preferably belongs to the at least two —C(O)O— groups (ester groups), which interrupt the carbon chain of the residue R* in the present invention.

As mentioned above, the hydrocarbon chain of R* can further be interrupted by oxygen atoms (ether groups) or sulfur atoms (thioether groups). The hydrocarbon units between the ether groups, thioether groups or ester groups are preferably alkylene units and can, but do not have to be, substituted by one or more substituents which are preferably selected from among hydroxyl groups, carboxylic acid groups, phosphate groups, phosphonic acid groups, phosphoric acid groups and (preferably primary or secondary) amino groups or amino acid groups.

Each of the OH groups of the compound $R^*(OH)_x$ can be an alcohol group or a part of a carboxylic acid group. Compounds with x>1 can contain alcohol groups as well as carboxylic acid groups, or can be polyalcohols or polycarboxylic acids.

The silanes/silane blends and/or silicic acid polycondensates can be polymerized organically due to the presence of organically polymerizable groups so that they can form an additional organic cross-linking structure besides the inorganic three-dimensional skeleton composed of Si—O—Si units.

In a first specific embodiment of the invention, the compound $R^*(OH)_x$ is a monovalent alcohol or a monovalent carboxylic acid having the formula R¹'OH, wherein R¹' is a monovalent residue which has to satisfy all other conditions for R* mentioned above. If reacted with a silane (A), silanes having the formula (1) are obtained $$R^1_a SiR_{4-a} \quad (1)$$

wherein R¹ represents the residue R¹'O which is linked to the silicon atom via an oxygen atom of the OH group of the starting compound R¹'(OH). In the present invention, the reaction is carried out in a manner that the silanes of formula (1) have at least one, preferably several (more preferably about two on average) substituents R¹ per silicon atom. The hydrocarbon-containing chain having a variable length of the residue $R^1$ has above-mentioned features as regards the number of ester groups, length of the individual hydrocarbon units and the organic polymerizable groups. The index a in these silanes is selected from among 1, 2, 3 and 4, wherein the silanes of formula (1) are usually blends of silanes with different meanings of the index a, and the index a in the blend frequently has an average value of about 2.

The silanes of formula (1) can be converted via hydrolytic condensation reactions to silicic acid polycondensates in known manner.

In a second specific embodiment of the invention, the compound $R^*(OH)_x$ is a divalent compound having the formula $R^{2'}(OH)_2$, wherein $R^{2'}$ is a divalent residue which has to satisfy all requirements for $R^*$ mentioned above. It can be a dialcohol, a dicarboxylic acid or a compound with one carboxylic acid group and one alcohol group.

In the reaction of compounds $R^{2'}(OH)_2$ with the silane (A), blends of silanes are formed in which the residues of the compound $R^{2'}(OH)_2$ are either (i) linked to one or two silicon atoms via two oxygen atoms (these residues are denoted with $R^2$ hereinafter), or (ii) are linked to one silicon atom via only one oxygen atom while the second OH group remains free (these residues are denoted by R2"(OH) hereinafter), wherein the respective contents of the individual components can to a certain extent be controlled via the applied amount ratios. Individual components of these blends can be represented by the following formulae which do not in all cases represent the exact structural formulae, but should in part be understood as total formulae.

For example, monomeric silanes having the formula (2)

$$R^2SiR_2 \quad (2)$$

or formula (3)

$$R^2{}_2Si \quad (3),$$

dimeric silanes having the formula (4)

$$R^2Si_2R_6 \quad (4)$$

or the formula (5)

$$R^2RSi{-}O{-}SiRR^2 \quad (5)$$

or ring-shaped oligosilanes having the formula (6)

$$[R^2SiR_2]_n \quad (6)$$

or chain-shaped oligosilane having the formula (7)

$$R_3Si[(R^2)_2SiR_2]_nSiR_3 \quad (7)$$

wherein n is a number which cannot be defined or adjusted more precisely and which is usually between about 4 and 12, preferably about 8, or chain-shaped oligosilanes having the formula (8)

$$R_2R^{2''}(OH)Si[(R^2)_2SiR_2]_nSiR^{2''}(OH)R_2 \quad (8)$$

wherein n is as mentioned for formula (6) and (7), or chain-shaped oligosilanes having the formula (9)

$$R_2R^{2''}(OH)SiR^2SiR^{2''}(OH)R_2 \quad (9)$$

or longer chain compounds can be formed.

With the exception of compound (4), (6), (7) and (8) and partly in compound (9), the residue $R^2$ in all of these compounds is linked to only one silicon atom via two oxygen atoms. Such structures are preferably formed when the two hydroxyl groups of compound $R^{2'}(OH)_2$ are bound to carbon atoms which are vicinal or in 1,3-position to each other so that a linkage via the oxygen atoms of both hydroxyl groups to only one silicon atom is preferred (a 5- or 6-membered ring is respectively formed).

It should be noted that the term "silane" in the present invention does not only comprise monomeric silanes but also the aforementioned disilanes and oligosilanes.

If the compound of formula $R^{2'}(OH)_2$ is used in a large molar excess with respect to the silane (A), silanes having the formula (10) can be formed, as the case may be,

$$[R^{2'''}(OH)]_aSiR_{4-a} \quad (10),$$

wherein $R^{2'''}$ has above meaning. It can be recognized that these silanes are comparable to the silanes of formula (1) except that the residue $R^{2'''}$ in structures (10) always carry a free hydroxyl group.

In the present invention, the molar ratio of the alcohol represented by formula $R^{2'}(OH)_2$ to the silane (A) is preferably around 2:1.

It can be beneficial to use a mixture of at least the compounds of formula $R^1OH$ and formula $R^{2'}(OH)_2$. Such a mixture can readily be obtained in case of a suitable reaction process of the respective starting materials. This is for example the case when alcohols having the formula $R^1OH$ and formula $R^{2'}(OH)_2$ are formed by reaction of a triol with an activated carboxylic acid as shown in the examples below, wherein, depending on the applied proportions, mixtures of the monoesters and diesters are formed, possibly in admixture with unreacted triol.

The silanes or silane blends obtained in the aforementioned reaction can of course also be converted to silicic acid polycondensates via hydrolytic condensation reactions in a known manner, except for compound (3) in which the (only) silicon atom has no hydrolyzable group R anymore. As long as compound (3) is contained in the blend, it can still be incorporated into the resulting organic network via its organic polymerizable groups in a subsequent organic polymerization reaction, as will be explained in more detail below.

In further embodiments of the invention, the compound $R^*(OH)_x$ is a multivalent compound having the formula $R^{x'}(OH)_x$, wherein x=3 or 4 or a higher number, wherein the residue $R^{x'}$ has x bonds and further all conditions for $R^*$ mentioned above have to be satisfied. Because of the steric relations, in the reaction of such compounds for x=3 with the silane, predominantly silanes corresponding to the silanes (2) to (10) are formed, comprising residues $R^3$ and/or $R^{3'''}$ instead of residues $R^2$ and/or $R^{2'''}$, which have an additional free hydroxyl group as compared to the residues $R^2$ and/or $R^{2'''}$. Also in these embodiments, the molar ratio of the compound with formula $R^{x'}(OH)_x$ to the silane is preferably in the range of about 2:1.

Figure 1:
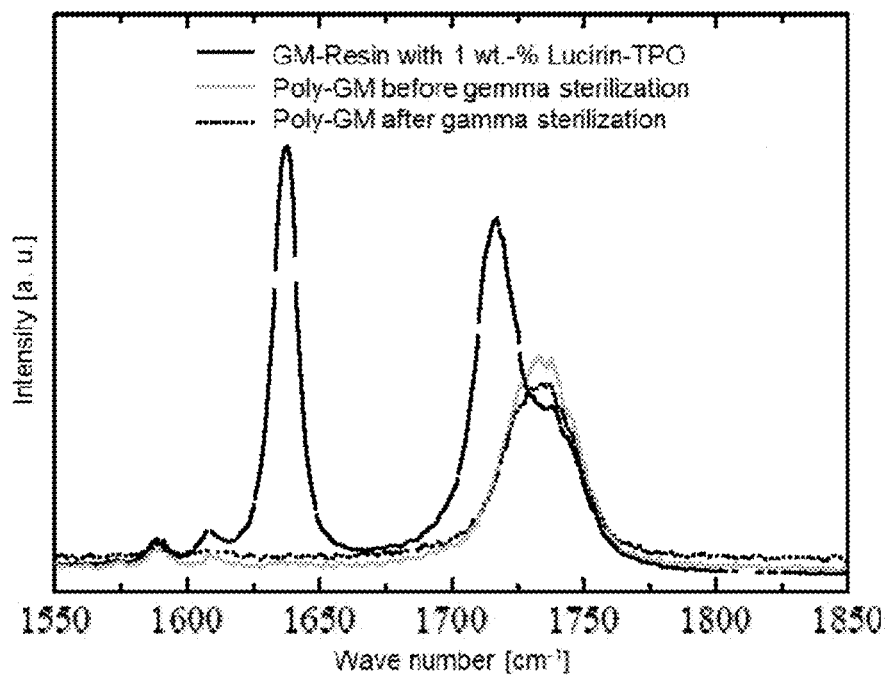
FIG. 1 shows μ-Raman spectrum of GM-Resin with 1 wt. -% Lucirin-TPO compared to Poly-GM before gemma sterilization vs Poly-GM after gamma sterilization.
Figure 2:
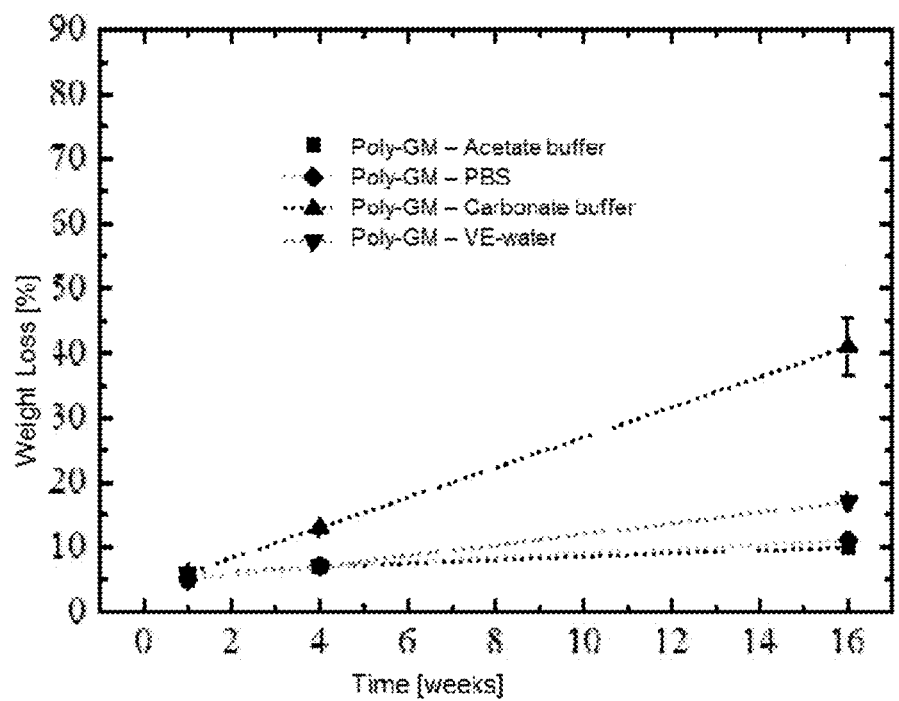
FIG. 2 shows the Weight Loss in [%] versus the storage Time in weeks for Poly-GM with an Acetate buffer, a PBS, Carbonate buffer, and a VE-water.
Figure 3:
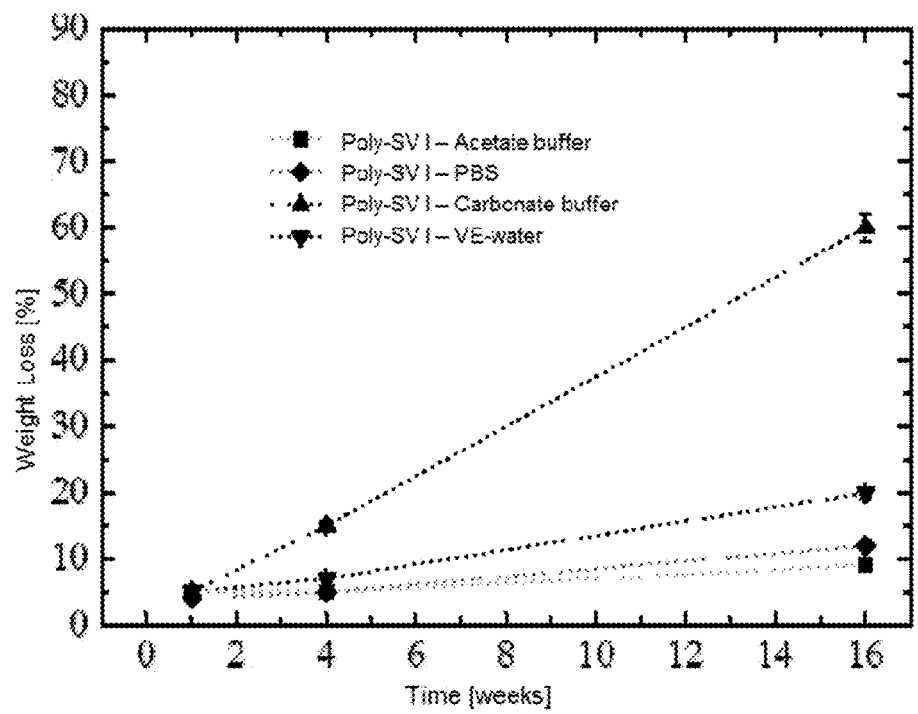
FIG. 3 shows the same for Poly-SV I with an Acetate buffer, a PBS, Carbonate buffer, and a VE-water.
Figure 4:
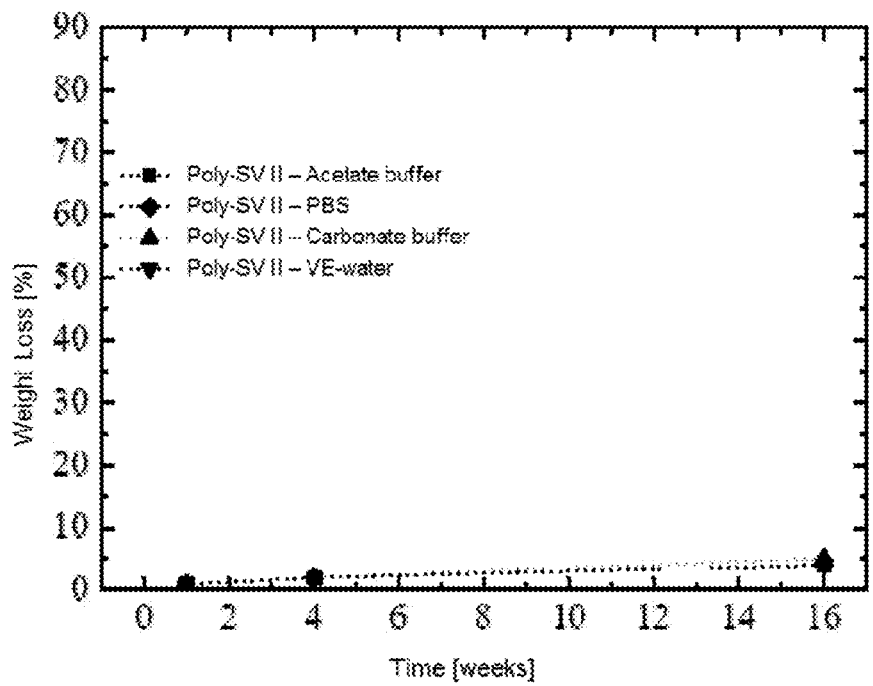
FIG. 4 shows the same for Poly-SV II with an Acetate buffer, a PBS, Carbonate buffer, and a VE-water.
Figure 5:
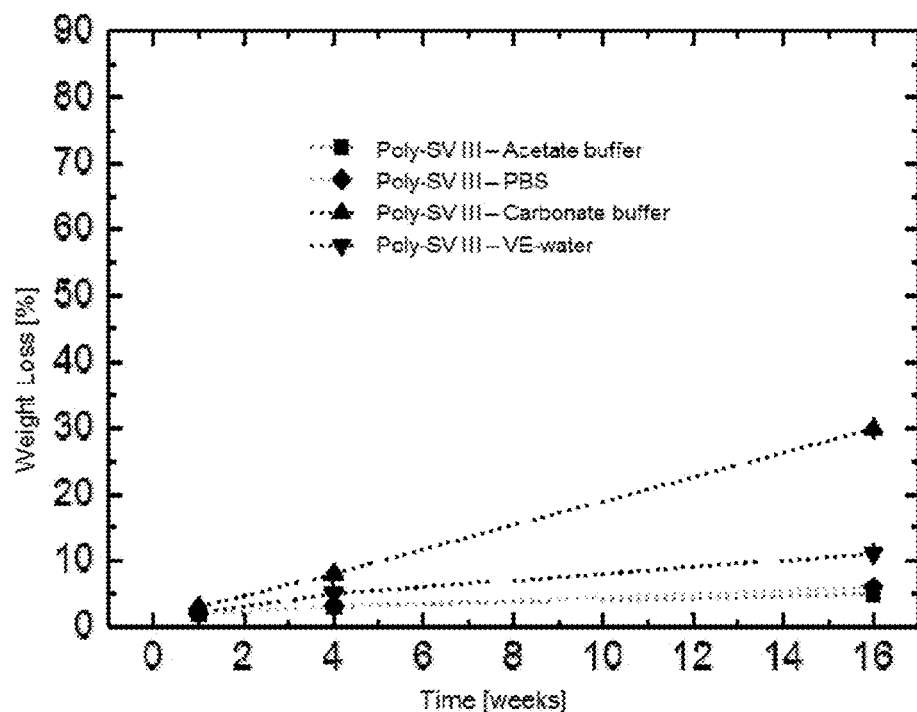
FIG. 5 shows the same for Poly-SV III with an Acetate buffer, a PBS, Carbonate buffer, and a VE-water.

Hereinafter, the present invention is illustrated in more detail using a schematic representation of a silane represented by formula (1) according to the invention. One of the substituents $R^1$ as in formula (1) is shown which is linked through an ether oxygen atom to the silicon atom. This oxygen atom is part of a polyethyleneglycol group having n ethyleneglycol units and therefore n alkylene groups with two carbon atoms each. The final unit is esterified with ethylene dicarboxylic acid, the second carboxylic unit of which is again esterified with ethyleneglycol (optionally substituted with an arbitrary substituent R", which may preferably be $CH_3$, COOH or $CH_2OH$), wherein the second OH group is esterified with methacrylic acid to eventually obtain a derivative of 4-[2-(methacryloyloxy)ethoxy]-4-oxo-butanoic acid (MES). Thus, the group is unbranched (except for a branch caused by R", as the case may be) und has a methacryl group at the terminal remote from the silicon atom, which can be organically polymerized via its C=C double bond. It should be clear that the substituent R" in this schematic representation is only exemplary and such substituents can (also) be present at any (other) sites. It is also clear that an alternative to the silane represented below is a silane in which n is 0, and not 3 or 6 as displayed, but which otherwise comprises all below-mentioned components. In such a silane with n=0, $R^1$ is linked to the silicon atom through a carboxyl group oxygen atom.

arranged rather rigidly with respect to each other due to the preceding hydrolytic condensation; a higher-ranking cross-linking of a continuous multitude of methacrylate groups is therefore unlikely. If materials comprising additional OH substituents or COOH substituents or the like on the respective hydrocarbon chains are used, molecules may be formed which occur as intermediate products in the human body, such as lactic acid or citric acid, which can be introduced into the metabolism. The remaining, essentially inorganic residues are presumably essentially fragments with Si—O—Si linkages carrying external hydroxyl groups.

Through hydrolysis and condensation of the silane shown above (here, represented by formula (1) with R=OAc, i.e. $CH_3C(O)O$, a resins is formed (an organic modified silicic acid polycondensate) which is denoted as "GM-Resin" hereinafter:

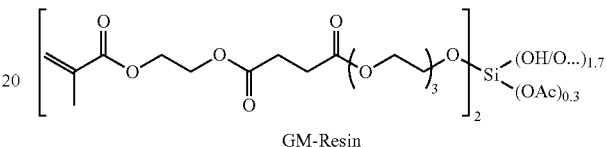

GM-Resin

The substitution of the silicon with two of the organic substituents $R^1$ is an average value; the starting "silane" for the resin usually consists of a blend of different silanes in

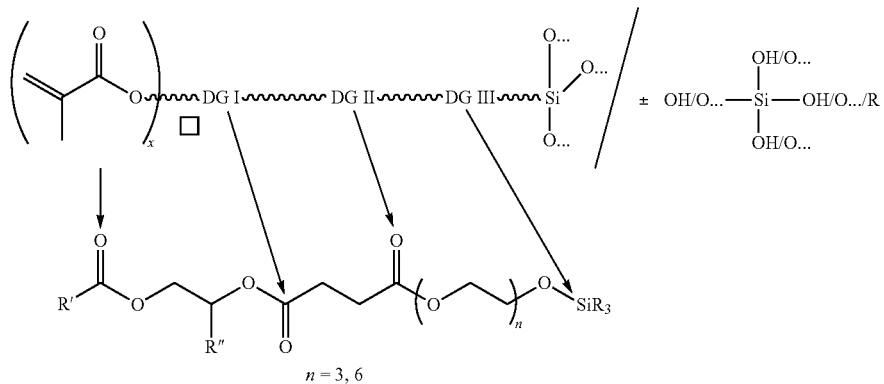

$n = 3, 6$

The two carboxylic acid ester groups in this group can be hydrolyzed and are here denoted as DG I and DG II. The ester bond between the methacrylic acid and the ethylyenglycol, which is optionally substituted with R", can also be cleaved by hydrolysis. Under hydrolyzing conditions, there is also a cleavage of the Si—O bond at "DG III". A material is thereby for the first time provided which can also be degraded at the coupling site of the organic group to the silicon. Moreover, polyether groups such as mentioned by E. M. Christenson et al. in Wiley InterScience on 2. June 2004 under DOI: 10.1002/jbm.a.30067, can in some cases be oxidatively cleaved in vivo.

It is clear from above explanations that the provision of only short hydrocarbon chains interrupted by ester groups (—C(O)O—) and possibly oxygen atoms and/or sulfur atoms results mainly in low molecular products in case of hydrolysis, which are normally physiologically harmless as such. In the above example, e.g. succinic acid and a cross-linked polymethacryl fragment which is also toxicologically harmless due to its cross-linked state, are formed. The latter can be assumed to be relatively low-molecular depending on the cross-linking conditions because the silane molecules are which partially none, partially one, two, three or four of these organic groups are linked to one silicon atom, wherein there are two of the organic groups on average per silicon atom. The number of OAc groups (acetyl groups) at the silicon atom is also a statistical value (the acetyl groups in the example are derived from the starting material, silicon tetraacetate, and remain with about the same content even under hydrolysis conditions). The hydroxyl groups formed by hydrolysis of OAc groups are converted to Si—O—Si bridges under the conditions of a hydrolytic condensation.

The resin denoted above by GM-Resin and other resins were organically polymerized and their mechanical properties were evaluated in this state. As a result, the length of the substituent $R^1$ of the invention has an effect on the tensile strength and the E modulus (Young's modulus): the longer the substituent, the softer the material.

This can be recognized from a comparison of the polymerized GM-Resin ("Poly-GM" hereinafter) with the polymerization product of a resin, which is also according to the invention and differs only in that six instead of three ethyleneglycole units are contained in the group:

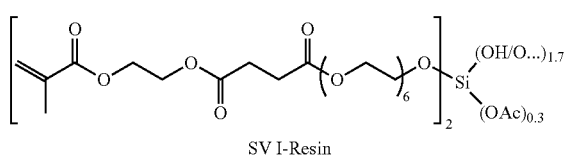

SV I-Resin

This resin is denoted as SV I-Resin and the polymerization product thereof as Poly-SV I. The number of organic polymerizable C=C double bonds per substituent $R^1$ again has a strong effect on the mechanical properties: if this substituent is branched and if both branching terminals each comprise an organic polymerizable C=C double bond, the tensile strength values and E modulus values increase by more than an order of magnitude. This can be shown by a comparison of the values for Poly-GM and Poly-SV I with the polymerization product of a further resin according to the invention having the following composition:

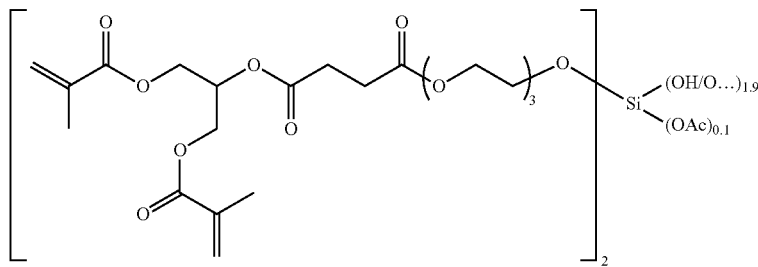

SV II-Resin

This resin is denoted as SV II-Resin and the polymerization product thereof as Poly-SV II.

A likewise significant increase of the strength is obtained by an increase of the amount of inorganic cross-linking groups: if a silane used for the GM resin is not subjected as such to a hydrolytic condensation, but in combination with a further silane having a multitude (e.g. two to three) of hydrolytically condensable residues and otherwise only short organic substituents, for example with a partially hydrolyzed/condensed ethyltriacetoxysilane or a partially hydrolyzed/condensed tetraethoxysilane, resulting in e.g. the following material denoted as SV III-Resin, Moreover, the condensation degree of the resins has an effect on the mechanical properties to a certain extent: the more condensation, i.e. the more Si—O—Si bridges are present, the harde the product.

The values determined for the above-mentioned materials can be taken from the following table 1 where they are compared to corresponding values of natural tissue.

TABLE 1

| Synthesized materials | Tensile strength [MPa] | Natural tissue | Tensile strength [MPa] |
| --- | --- | --- | --- |
| Poly-GM | 4.3 ± 0.2 | bladder | 0.27 ± 0.14 |
| Poly-SV I | 1.8 ± 0.2 | blood vessel | 1.4-11.1 |
| Poly-SV II | 30.3 ± 3.1 | aorta | 1.72 ± 0.89 |
| Poly-SV III | 12.5 ± 0.6 | cartilage | ~5 |

TABLE 1-continued

| Synthesized materials | E modulus [MPa] | Natural tissue | E modulus [MPa] |
| --- | --- | --- | --- |
| Poly-GM | 43.5 ± 2.6 | soft tissue | 0.4-350 |
| Poly-SV I | 18.9 ± 1.1 | | |
| Poly-SV II | 615 ± 116 | hard tissue | 10-1500 |
| Poly-SV III | 109 ± 11.1 | | |

It can be recognized that the materials of the present invention allow a specifically intended adaption of the mechanical values to certain tissues. Since both the inorganic and the organic cross-linking density can be adjusted,

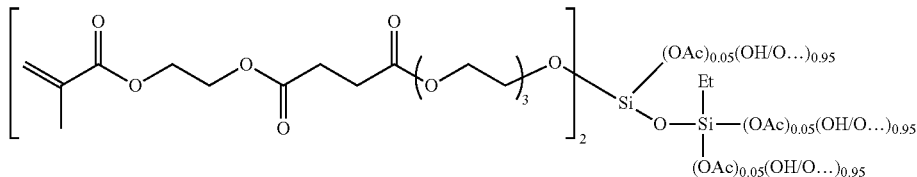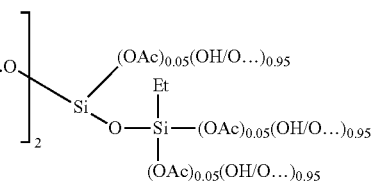

SV III-Resin the mechanical values of the polymerized material ("Poly SV III") increase to about the threefold as compared to the pure polymerized Poly-GM.

a person of ordinary skill in the art can precisely obtain the desired values by an appropriate selection within the parameters described by the present invention.

The organic polymerizable groups (such as the C═C double bonds) can, as the case may be, be polymerized in the resin mass/bulk, but can in particular also be polymerized at structurally desired points in a resin material bath. In this manner, the condensed resin can be provided as a mass (liquid or paste-like) and can be polymerized in a desired shape or a desired pattern for example by 2 photon polymerization ("TPA processing"). To this end, an irradiation with laser light is performed in a known manner, as described for example in WO 2011/098460 A1. Instead, a structuring using other techniques can also be performed, for example by a so-called rapid prototyping, where the desired shape is produced by sequential irradiation of a surface bath layer and subsequent lowering of the solidified layer.

During the irradiation, essentially all organic C═C double bonds are reacted, independently from whether the irradiation is carried out in a structured manner or throughout the whole material. This can be demonstrated with the help of the µ-Raman spectrum displayed in FIG. 1 (dark graph: condensed GM-Resin before polymerization, with 1% admixed photoinitiator. The two almost superposed light graphs show the irradiated resin, before and after an additional irradiation with γ-rays. The wavenumbers [cm$^{-1}$] are plotted on the abscissa and the intensity is plotted on the ordinate in relative units (arbitrary units, "a.u.")). The irradiated resin was examined before and after an additional irradiation with γ-rays because gamma irradiation is the most simple and most frequently applied sterilization in the medical sector—the suitability in view of this aspect is another advantage of the present invention. The high conversion rate of the organic polymerizable groups contributes to the good biocompatibility because methacrylate monomers, which would be generated in case of a degradation of unpolymerized structures, are normally toxic molecules; therefore, it is highly desirable to suppress their formation in the degradation.

Figure 6:
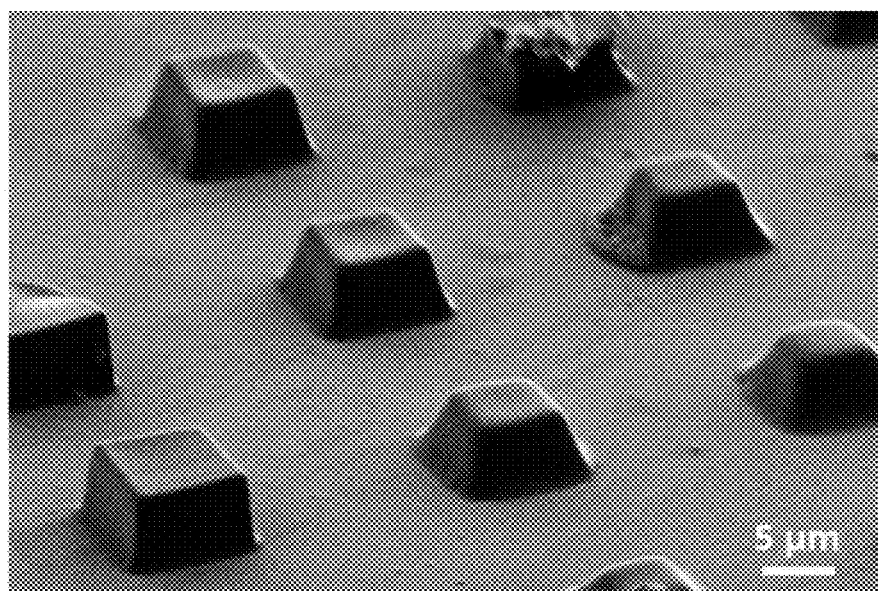
FIG. 6 shows a three-dimensional structure produced according to this invention.

The unpolymerized material can then be washed away. A three-dimensional structure produced in this manner is shown in FIG. 6. Due to this capability of being structured, the materials of the present invention are well suitable for the production of fine objects such as scaffolds. Moreover, the resistance against gamma radiation makes the objects capable of being sterilized.

The cross-linking in the materials can be modified/enhanced. This specific form of post-curing does not (or not only) make use of the polymerization reaction (polyaddition) of the organic polymerizable groups as such, as explained above. When the organic polymerizable groups are C═C double bonds or ring-opening systems such as epoxides, a reaction of silicic acid polycondensates containing these double bonds with diamines or higher amines or dithiols or higher thiols via a Michael addition (thiol-ene-reaction or the analogous reaction with amines) is possible. This can be achieved with diamines, triamines, tetraamines or even higher functionalized amines or mercaptanes (thiols), wherein the reaction with amines in case of C═C double bonds as organic polymerizable groups is (only) possible when they are in their activated form, for example as acrylic groups or methacrylic groups (including (meth) acrylate groups). The polymerization of the remaining C═C double bonds or ring-opening systems such as epoxide groups is then carried out as described above.

It goes without saying that the in this embodiment, the addition of the thiol compound or amine compound has to be done with a molar deficiency of SH groups and/or amino groups with respect to the organic polymerizable groups, so that organic polymerizable groups remain after the Michael addition which can be subjected to the organic polymerization reaction.

In an alternative embodiment of the cross-linking reaction, the cross-linking by the aforementioned multiple functional mercaptanes and/or amines can completely replace the polymerization reaction of the organic polymerizable groups. In this case, the thiols or amines are admixed at least in such an amount that one mercapto group or amino group is available per organic polymerizable group, so that all these groups react with the thiols and/or amines via the cross-linking reaction.

The following are examples of polyfunctional compounds which can be used for bridging both via a ring-opening of reactive cyclic ethers and via the reaction with C═C double bonds:

Examples for multifunctional thiols are: trimethylolpropanetri-(3-mercaptopropionate) (TMPMP); trimethylolpropane-trimercaptoacetate) (TMPMA); pentaerytritoltetra(3-mercaptopropionate) (PETMP); pentaerytritoltetramercaptoacetate) (PETMA); glycoldimercaptoacetate; glycoldi(3-mercapto-propionate); ethoxyliated trimethylolpropanetri(3-mercaptopropionate); biphenyl-4-4'-dithiol; p-terphenyl-4,4"-dithiol; 4,4'-thiobisbenzenethiol; 4,4'-dimercaptostilbene; benzene-1,3-dithiol; benzene-1,2-dithiol; benzene-1,4-dithiol; 1,2-benzenedimethanethiol; 1,3-benzenedimethanethiol; 1,4-benzenedimethanethiol; 2,2'-(ethylendioxy)diethanethiol; 1,6-hexanedithiol; 1,8-octanedithiol; 1,9-nonanedithiol, dipentaerythritolhexa(3-mercaptopropionate) (DiPETMP, commercially available as THIOCURE®)

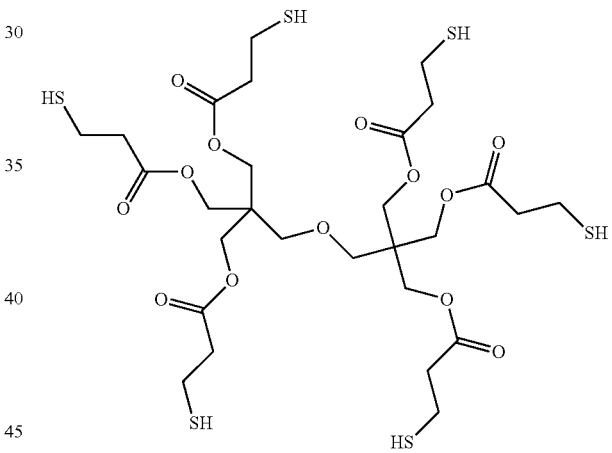

tris[2-(3-mercaptopropionyloxy)ethyl]isocyanurate (commercially available as THIOCURE® TEMPIC)

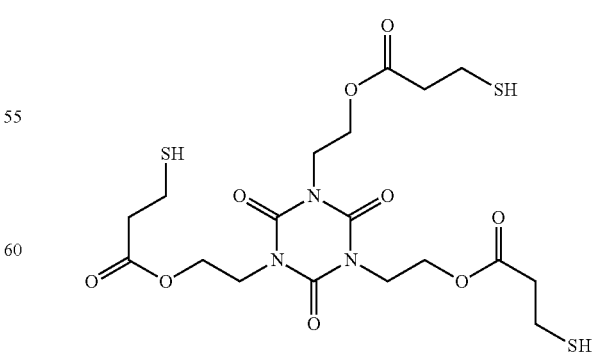

ethoxylated trimethylolpropane-tri-3-mercaptopropionate (commercially available as THIOCURE® ETTMP 700)

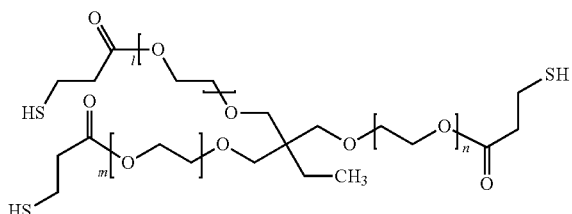

glycerin-1,3-dithioglycolate or glycerin-1,2-dithioglycolate

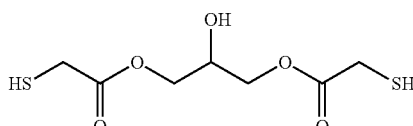

The amines are normally primary amines because these show a higher reactivity. However, secondary amines are also comprised by the present invention. Examples for multifunctional amines are: diaminoacetone, diaminoacridine, diaminoadamantane, diaminoanthraquinone, benzidine, diaminobenzoic acid, phenylenediamine, diaminobenzophenone, diaminobutane, diaminocyclohexane, diaminodecane, diaminodicyclohexylmethane, diaminomethoxybiphenyl, diaminodimethylhexane, diaminodiphenylmethane, diaminododecane, diaminoheptane, diaminomesitylene, diaminomethylpentane, diaminomethylpropane, naphtyhlenediamine, diaminoneopentane, diaminooctane, diaminopentane, diaminophenanthrene, diaminopropane, diaminopropanol, diaminopurine, diaminopyrimidine. If secondary amines should be used, they contain a group NHR*, wherein R* usually represents a mostly shorter chain alkyl group (e.g. $C_1$-$C_8$, preferably $C_1$-$C_4$) or an optionally substituted aryl group (e.g. phenyl group) or aralkyl group, instead of the group NH2, for example in above-mentioned compounds.

The thiol addition is normally carried out in the presence of an initiator, as known in the art, while the amine addition is also possible without an initiator.

If the cross-linking replaces the polymerization reaction, a slightly loose organic network is formed because S-(hydrocarbon)-S bridges or N-(hydrocarbon)-N bridges are formed.

If the thiols and/or amines used for the Michael addition comprise a degradable skeleton, for example comprising ester bridges and/or ether bridges, as is the case in the thiols mentioned above by their formulae, this additional transverse cross-linking can result in an increased mechanical stability or other mechanical modifications of the end products, without reducing the degradable part of the systems and thus the degradability. Accordingly, the mechanical properties (e.g. the E modulus) can be finely and determinedly adjusted through admixture of transversely cross-linking thiols and/or amines. The degradability of the organic polymer structure can even be increased by the addition of thiol and/or amine, as can be seen from the examples following further below.

The cross-linking degree can also be modified by adding or the presence of comonomers, provided these comonomers comprise at least two copolymerizable groups such as C=C double bonds or ring-opening systems like epoxide groups. The copolymerization with such monomers can be carried out alternatively to or in addition to the Michael addition. The comonomers are copolymerized in the organic polymerization of the resin. The product then has a relatively lower amount of Si—O network with respect to the organic network structures.

In a particularly beneficial variant of the invention, it is possible to benefit from the fact that polylkyleneglycoles can be used to obtain hydroxyl group-containing organic residues which can be reacted with a silicon compound to the silanes of the present invention. These are reacted for example with an activated carboxylic acid, such as an acid chloride containing the organic polymerizable group (e.g. a (meth)acrylate) on one end, to a glycolemonoester, and a corresponding diester can be produced as a side product. If this is not removed, it remains in the reaction mixture in the reaction with the silicon compound and is copolymerized during the curing of the resin.

In view of the use of the materials of the present invention for scaffolds and the corresponding requirement of biodegradability under physiological conditions, the degradation properties of organically cross-linked materials according to the invention was examined. The pH can vary between 1 and 9 in the body, depending on the region. An examination in different pH ranges is therefore expedient.

The organically polymerized materials were stored in different buffers with pH values between 4.65 (acetate buffer) and 9.6 (carbonate bicarbonate buffer). The ordinate in FIGS. 2 to 5 show the weight loss in [%], the abscissa shows the storage time in weeks. The pH of the surrounding medium had a strong effect on the degradation rate. For the polymers Poly-GM, Poly-SV I und Poly-SV III, the strongest weight loss was observed in a carbonate bicarbonate buffer (about 40-60% after 16 weeks); the weight loss was considerably less in completely desalted water (pH 6.5-7.0 at 20° C.), phosphate buffered saline ("PBS", pH 7.4 and in acetate buffers having a pH of 4.65 at 20° C. (in the latter cases about 5-10%, respectively). On the other hand, Poly-SV III is only slowly degraded under slightly alkaline conditions, while the degradation in acid conditions is comparable with the degradation rates of the other polymers.

Based on these four investigated examples of resins without added thiol it can be shown that a weight loss was observed in case of all organically cross-linked hybrid polymers in the chosen period of four months, while the degradation rate/speed was strongly influenced by the structural differences in the polymers. It can be realized that the degradation is not only influenced by the pH of the medium but also by variations in the structure of the hybrid polymers. The higher the number of hydrophilic groups (such as ethylene glycol units) contained, the faster the degradation. On the other hand, a higher organic (transverse) cross-linking and/or a higher content of inorganics and a higher condensation degree (a higher inorganic cross-linking) slows down the hydrolysis rate. These observations can be used to select tailored materials for specific uses.

It is also noteworthy that the measured degradation rates were essentially constant over the elapsed time. Even if the values show that the degradation did not proceed fast, it is still significant since a biodegradation mostly should take effect only within a rather long period of time: first, injuries should have healed and/or cells should have adhered and proliferated before the mechanical support (implant, scaffold) is allowed to disappear by degradation.

The examinations of the degradation of the polymer composed of a resin to which a polythiol compound has been added were carried out in a carbonate buffer solution at 37° C. The weight losses after one week were about 34%, about 74% after 4 weeks and about 84% after 16 weeks. Hence, the addition of an at least difunctional compound to the resin, which effects a thiol-ene addition reaction or another Michael addition reaction, can drastically increase the degradation rate.

The content of organically cross-linkable groups can be adjusted within a wide range in the materials of the present invention. When the organic cross-linking is relatively low, it can be expected that upon degradation of the hybrid polymers, structures which otherwise could not be degraded, such as polymethacrylate structures having a relatively low molecular weight, can be freed from the polymer compound and be resorbed, e.g. by macrophages, and degraded by digestion. Polymer structures which are highly dominated organically, which are obtained by addition of copolymerizable organic difunctional and thereby bridge-forming monomers, are even directly and rather quickly degradable.

It could further be shown that Upcyte endothelian cells adhere well to organically polymerized Poly-GM and other materials of the present invention while not losing their characteristic morphology. Using immunostaining (with anti-tubulin β and DAPI), a cell division of cells adhering to this material could be shown.

The present invention therefore provides a new class of biodegradable and biocompatible organic-inorganic hybrid polymers with mechanical properties that can be adapted to those of specific tissues, and which, by means of two-photon polymerization (2-PP) or by means of other methods, can be polymerized in bulk or organically in a structured manner and show a high conversion degree of the organically polymerizable groups.

The biodegradability which is determined via the weight loss depends on the surrounding pH. Further, it can be affected by modifying the polymer structure.

The mechanical properties can be adjusted within a certain range and can thereby be adapted to those of native tissue. The adjustment mainly takes place by varying the content of organically polymerizable groups, the length of the respective group and content of inorganic material.

Three-dimensional, finely structured objects can in particular be produced by 2-PP polymerization which further makes the invention suitable for the production of scaffolds.

Light-induced polymerization results in hybrid polymers having a high degree of conversion of the C=C double bonds and thereby results in degradation products which are essentially free from toxically relevant components. Irradiation with gamma rays can be used for sterilization purposes since such an irradiation does not adversely affect the polymerized material.

The use of the materials of the present invention is not restricted to the aforementioned applications. They can generally be utilized for various purposes such as bulk materials, fibers, composites, cements, adhesives, casting compounds, coating materials, the use in (reaction) extruders in the field of multiphoton polymerization. A use for medical applications (such as implants, bone substitute material, bone cement) is particularly significant.

The following examples illustrate the production of the individual aforementioned materials.

Synthesis of 4-[2-(methacryloyloxy)ethoxy]-4-oxo-butanoic acid-chloride (MES-Cl)

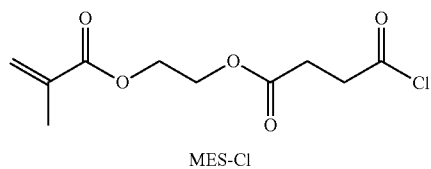 [SMILES: C=C(C)C(=O)OCCOC(=O)CCC(=O)Cl]

MES-Cl

The synthesis of 4-[2-(methacryloyloxy)ethoxy]-4-oxo-butanoic acid-chloride (MES-Cl) was carried out according to T. E. Kristensen et al., *Org. Lett.* 2009, 11, 2968 with slight modifications (reversed order of addition and lower excess of thionylchloride): to 69.83 g (303.3 mmol, 1.0 equiv.) 4-[2-(methacryloyloxy) ethoxy]-4-oxo-butanoic acid (MES), 72.62 g (610.4 mmol, 2.0 equiv.) thionylchlorid were added under nitrogen atmosphere, stirring and reflux. The clear solution was stirred for 30 min at 30° C. and 1 h at 50° C. Then, the excess thionyl-chloride and the volatile components were removed under reduced pressure and/or oil pump vacuum.

Yield: 75.88 g (305.2 mmol, 100%)

$M_{cal.}$ ($C_{10}H_{13}ClO_5$)=248.66 g/mol $^1$H-NMR (400.1 MHz, CDCl$_3$):

δ [ppm]=1.95 (s, 3H, CH$_3$), 2.70-2.73 (t, 2H, CH$_2$CH$_2$C(O)Cl, $^3J_{HH}$=6.52 Hz), 3.22-3.25 (t, 2H, CH$_2$CH$_2$C(O)Cl, $^3J_{HH}$=6.53 Hz), 4.35-4.40 (m, 4H, OCH$_2$CH$_2$O), 5.61-5.62 (m, 1H, H$_2$C=, cis), 6.13 (s, 1H, H$_2$C=, trans).

$^{13}$C-NMR (100.6 MHz, CDCl$_3$):

δ [ppm]=18.26 (CH$_3$), 29.24 (CH$_2$CH$_2$C(O)Cl), 41.69 (CH$_2$CH$_2$C(O)Cl), 62.19 and 62.85 (OCH$_2$CH$_2$O), 126.23 (H$_2$C=), 135.84 (=C(CH$_3$)C(O)OR), 167.09 (=C(CH$_3$)C(O)OR), 170.67 (C(O)OR) and 172.96 (C(O)Cl).

FT-IR: ṽ [cm$^{-1}$]=2961 (m, v(CH)), 1794 (vs, RCOCl v(C=O)), 1721 (vs, v(C=O)), 1637 (m, v(C=C)), 712 (m, v(C—Cl)).

μ-Raman: ṽ [cm$^{-1}$]=2955 and 2928 (vs, v(CH)), 1793 (w, RCOCl v C=O)), 1714 (s, v (C=O)), 1639 (s, v C=C)), 707 (m, v (C—Cl)), 434 (s, v C—Cl)).

Synthesis of 4-[2-(methacryloyloxy)ethoxy]-4-oxo-butanoic acid-triethylene glycole ester (MES-TEG)

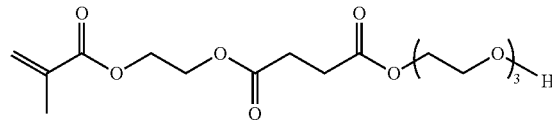

MES-TEG

An instruction of Wiseman et al., *J. Am. Chem. Soc.* 2005, 127, 5540 served as orientation for the synthesis of 4-[2-(Methacryloyloxy)ethoxy]-4-oxo-butanoic acid-triethylene glycole ester (MES-TEG): under a nitrogen atmosphere, 47.99 g (319.6 mmol, 3.2 equiv.) triethylene glycole (TEG) were dissolved in 100 ml dichloromethane and 9.17 g (115.6 mmol, 1.1 equiv.) pyridine were added thereto. 24.81 g (99.8 mmol, 1.0 equiv.) MES-Cl were added to the iced colorless solution under stirring. The mixture was stirred for 24 h at 30° C. and then 800 ml cold ethyl acetate were added, whereupon pyridine hydrochloride was precipitated as a white precipitate, which was removed in the subsequent extraction. The organic phase was purified by washing it three times with 200 ml cold water, respectively, and dried over sodium sulfate. The solvent was removed by distillation, the product was removed of volatile components for 3 h in an oil pump vacuum, and 0.2 wt.-% hydroquinone methylether (HQME) was added for stabilization. Insoluble components were removed by filtration using a syringe filter having a pore size of 5 μm. The product was stored under stirring in a PE bottle until further use.

Crude yield: 37.34 g

In the crude yield, the content of disubstituted triethylene glycole (MES$_2$TEG), produced as a by-product in the synthesis, when both OH-groups are esterified, is not yet considered. This content was determined using a $^1$H-NMR-spectrum. To this end, a signal at ≈3.60 ppm, corresponding to the CH$_2$ group in immediate vicinity to the alcohol functionality in MES-TEG and which is generated only by the main product, is defined as a reference. From the ratio of the integral for this signal to those of the remaining signals, formed by the superposition of main product and by-product, the content of MES$_2$TEG can be calculated, and is ≈15 mol-%. Since the by-product is harmless in the further reaction, the mixture was not further separated. However, this is possible without problem, if necessary, for example by chromatographic separation wherein silica gel or the like is used as a stationary phase and a common organic solvent is used.

If the content of MES$_2$TEG is subtracted, the yield is 29.18 g (80.5 mmol, 81%) M$_{cal.}$ (MES-TEG, C$_{16}$H$_{26}$O$_9$)= 362.37 g/mol $^1$H-NMR (400.1 MHz, CDCl$_3$):

δ [ppm]=1.95 (s, 3H, C$\underline{H}_3$), 2.67 (m, 4H, CC$\underline{H}_2$C$\underline{H}_2$C), 3.60-3.62 (m, 2H, (OCH$_2$CH$_2$)$_2$—OCH$_2$C$\underline{H}_2$OH), 3.65-3.73 (m, 8H, OC$\underline{H}_2$C$\underline{H}_2$OC$\underline{H}_2$C$\underline{H}_2$OC$\underline{H}_2$CH$_2$OH) 4.25-4.28 (m, 2H, OC$\underline{H}_2$CH$_2$(OCH$_2$CH$_2$)$_2$OH), 4.35 (s, 4H, OC$\underline{H}_2$C$\underline{H}_2$O), 5.60-5.61 (m, 1H, $\underline{H}_2$C=, cis), 6.13 (s, 1H, $\underline{H}_2$C=, trans).

$^{13}$C-NMR (100.6 MHz, CDCl$_3$):

δ [ppm]=18.28 ($\underline{C}$H$_3$), 28.92 (C$\underline{C}$H$_2$$\underline{C}$H$_2$C), 61.75, 62.34, 62.40, 63.74, 69.04, 70.33, 70.58 and 72.48 (4× O$\underline{C}$H$_2$$\underline{C}$H$_2$O), 126.13 (H$_2$$\underline{C}$=), 135.89 (H$_2$C=$\underline{C}$(CH$_3$)C(O)OR), 167.13 (=C(CH$_3$)$\underline{C}$(O)OR), 172.09 and 172.23 (O$\underline{C}$(O)CH$_2$CH$_2$$\underline{C}$(O)O).

FT-IR: ṽ [cm$^{-1}$]=3463 (m, ν(OH)), 2955 and 2876 (m, ν(CH)), 1737 (vs, ν(C=O)), 1637 (m, ν(C=C)).

μ-Raman: ṽ [cm$^{-1}$]=2955 and 2928 (vs, ν(CH)), 1714 (s, ν(C=O)), 1634 (s, ν(C=C)).

Synthesis of 4-[2-(methacryloyloxy)ethoxy]-4-oxo-butanoic acid-[3-hydroxy-2-hydroxymethylpropyl]-ester (MES-HPE)

Similar to the synthesis of MES-TEG, MES-HPE is produced by the reaction of 2 equivalents of the precursor MES-Cl with 2-(hydroxymethyl)propane-1,3-diol. A product mixture of monoester, diester and triester (the latter without free hydroxyl groups) is obtained. The monoester is an alcohol represented by the above-mentioned formula R$^{2'}$(OH)$_2$, the diester is an alcohol represented by the formula R$^{1'}$(OH).

4-[2-(Methacryloyloxy)ethoxy]-4-oxo-butanoic acid-glycerin ester (MES-GE)

Similar to the synthesis of MES-TEG, MES-GE is produced by the reaction of the precursor MES-Cl with glycerin. A product mixture of monoester, diester and triester is obtained. The monoester is shown below.

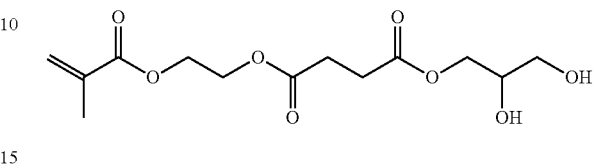

Synthesis of 4-[2-(methacryloyloxy)ethoxy]-4-oxo-butanoic acid-hexaethylene glycol ester (MES-HEG)

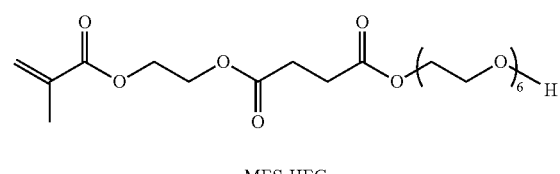

MES-HEG

The synthesis of 4-[2-(methacryloyloxy)ethoxy]-4-oxo-butanoic acid-hexaethylene glycol ester (MES-HEG) was carried out analogous to the reaction to obtain MES-TEG: under a nitrogen atmosphere, 85.90 g (304.3 mmol, 3.2 equiv.) hexaethylene glycol (HEG) and 8.71 g (110.1 mmol, 1.1 equiv.) pyridine were dissolved in 100 ml dichloromethane. 23.68 g (95.2 mmol, 1.0 equiv.) MES-Cl were added while cooling over ice and stirring. The mixture was stirred for 24 h at 30° C. and the product was isolated, purified and stabilized as described above for MES-TOG.

Crude yield: 32.74 g

The crude yield does not account for the content of disubstituted hexaethylene glycol (MES$_2$HEG), which is formed in the synthesis as a by-product. This content was determined with the aid of the $^1$H-NMR spectrum and is ≈5 mol-%. Since the by-product is not disadvantageous in the

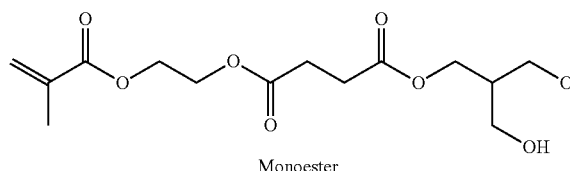

Monoester

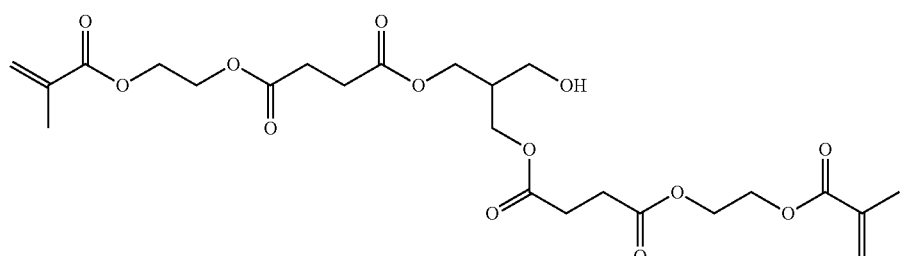

Diester further reaction, the mixture was not further purified. However, this could be done without problems, if necessary, for example by a chromatographic separation in which silica gel or the like serves as a stationary phase and a common organic solvent is used.

If the content of MES$_2$HEG is subtracted, the yield is 30.45 g (61.6 mmol, 65%).

$M_{cal.}$ (MES-HEG, $C_{16}H_{26}O_9$)=494.53 g/mol $^1$H-NMR (400.1 MHz, CDCl$_3$):

δ [ppm]=1.95 (s, 3H, C$\underline{H}_3$), 2.67 (m, 4H, CC$\underline{H}_2$C$\underline{H}_2$C), 3.60-3.62 (m, 2H, (OCH$_2$CH$_2$)$_5$CH$_2$C$\underline{H}_2$OH), 3.65-3.73 (m, 20H, OCH$_2$C$\underline{H}_2$(OC$\underline{H}_2$C$\underline{H}_2$)$_4$C$\underline{H}_2$CH$_2$OH), 4.23-4.26 (m, 2H, OC$\underline{H}_2$CH$_2$(OCH$_2$CH$_2$)$_5$OH), 4.35 (s, 4H, OC$\underline{H}_2$C$\underline{H}_2$O), 5.60-5.61 (m, 1H, $\underline{H}_2$C=, cis), 6.13 (s, 1H, $\underline{H}_2$C=, trans).

$^{13}$C-NMR (100.6 MHz, CDCl$_3$):

δ [ppm]=18.27 ($\underline{C}$H$_3$), 28.92 (C$\underline{C}$H$_2$$\underline{C}$H$_2$C), 61.70, 62.34, 62.38, 63.89, 69.03, 70.33, 70.56, 70.60 and 72.52 (7× O $\underline{C}$H$_2$$\underline{C}$H$_2$O), 126.12 (H$_2$$\underline{C}$=), 135.88 (=$\underline{C}$(CH$_3$)C(O)OR), 167.09 (=C(CH$_3$)—$\underline{C}$(O)OR), 172.04 and 172.19 (O $\underline{C}$(O)CH$_2$CH$_2$$\underline{C}$(O)O).

FT-IR: $\tilde{\nu}$ [cm$^{-1}$]=3466 (m, ν(OH)), 2873 (s, ν(CH)), 1737 (vs, ν(C=O)), 1637 (m, ν(C=C)).

µ-Raman: $\tilde{\nu}$ [cm$^{-1}$]=2935 and 2888 (vs, ν(CH)), 1722 (m, ν(C=O)), 1643 (m, ν(C=C)).

4-[2-(methacryloyloxy)ethoxy]-4-oxo-butanoic acid-[3-hydroxy-2,2-dihydroxymethylpropyl]-ester (MES-HDPE)

Also similar to the synthesis of MES-TEG, MES-HDPE is produced by the reaction of the precursor MES-Cl with 2,2-bis(hydroxymethyl)propane-1,3-diol. A product mixture of monoester, diester, triester and tetraester (the latter without free OH groups) is obtained. The monoester is shown below. It corresponds to the formula $R^{3'}(OH)_3$ illustrated above in more detail.

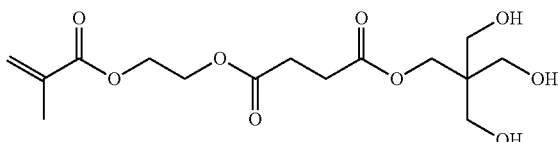

Synthesis of 4-{1,3-bis[(methacryloyl)oxy]propane-2-yloxy}-4-oxo-butanoic acid (GDM-SA)

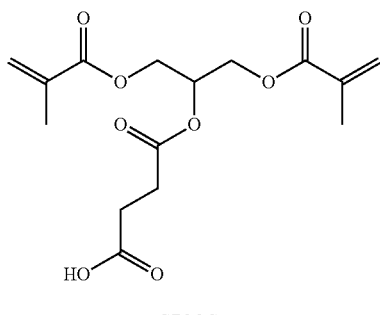

GDM-SA

The synthesis of 4-{1,3-bis[(methacryloyl)oxy]propane-2-yloxy}-4-oxo-butanoic acid (GDM-SA) was carried out based on an instruction of J. H. Liu, D. S. Wu, K. Y. Tseng, *Macromol. Chem. Physic.* 2004, 205, 2205. To a solution of 32.10 g (320.8 mmol, 1.0 equiv.) succinic anhydride (SA) and 665.3 mg (5.5 mmol, 0.02 equiv.) 4-dimethylaminopyridine (DMAP) as a catalyst in 300 ml 1,4-Dioxan, a further solution of 73.21 g (320.8 mmol, 1.0 equiv.) 1,3-glycerine dimethacrylate (GDM) and 109.5 mg (0.2 wt.-%) 4-hydroxyanisol (HQME) as a stabilizer in 120 ml 1,4-dioxane was added. The mixture was refluxed for 40 h at 80° C. and then cooled for 1 h to room temperature. Then, it was diluted with 460 ml cold dichloromethane, washed twice with 330 ml cold water, respectively, and dried over sodium sulfate. The solvent was removed under reduced pressure and volatile components were separated in an oil pump vacuum.

Yield: 96.97 g (295.4 mmol, 92%)

$M_{cal.}$(GDM-SA, $C_{15}H_{20}O_8$)=328.31 g/mol $^1$H-NMR (400.1 MHz, CDCl$_3$):

δ [ppm]=1.94 (s, 6H, C$\underline{H}_3$), 2.67 (m, 4H, CC$\underline{H}_2$C$\underline{H}_2$C), 4.19-4.45 (m, 4H, OC$\underline{H}_2$CHORC$\underline{H}_2$O), 5.36-5.45 (m, 1H, C$\underline{H}$) 5.61-5.62 (m, 2H, $\underline{H}_2$C=, cis), 6.13 (s, 2H, $\underline{H}_2$C=, trans).

$^{13}$C-NMR (100.6 MHz, CDCl$_3$):

δ [ppm]=18.23 ($\underline{C}$H$_3$), 28.73 and 28.78 (C$\underline{C}$H$_2$$\underline{C}$H$_2$C), 62.48 and 67.05 (O$\underline{C}$H$_2$CHOR$\underline{C}$H$_2$O), 69.51 ($\underline{C}$H), 126.51 (H$_2$$\underline{C}$=), 135.61 (=$\underline{C}$(CH$_3$)C(O)OR), 166.82 (=C(CH$_3$)$\underline{C}$(O)OR), 171.20 ($\underline{C}$(O)OR), 177.71 ($\underline{C}$(O)OH).

FT-IR: $\tilde{\nu}$ [cm$^{-1}$]=3265 (m, ν(OH)), 2961 and 2930 (m, ν(CH)), 1724 (vs, ν (C=O)), 1638 (m, ν (C=C)).

µ-Raman: $\tilde{\nu}$ [cm$^{-1}$]=2965 and 2932 (vs, ν C—H)), 1722 (s, ν C=O)), 1639 (s, ν C=C)).

Synthesis of 4-{1,3-bis[(methacryloyl)oxy]propane-2-yloxy}-4-oxo-butanoic acid-chloride (GDM-SA-Cl)

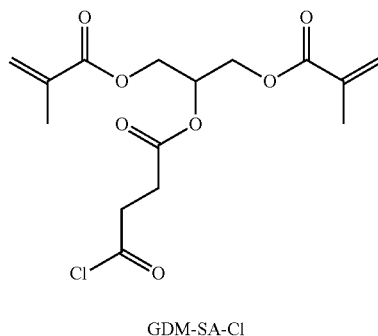

GDM-SA-Cl

The synthesis of 4-{1,3-bis[(methacryloyl)oxy]propane-2-yloxy}-4-oxo-butanoic acid (GDM-SA-Cl) was carried out analogous to the synthesis of MES-Cl: 90.30 g (275.0 mmol, 1.0 equiv.) GDM-SA were admixed with 65.27 g (551.4 mmol, 2.0 equiv.) thionylchloride under nitrogen atmosphere and stirring, and stirred for 30 min at 30° C. and 1 h at 50° C. Then, excess thionyl chloride and volatile components were removed under reduced pressure or in an oil pump vacuum.

Yield: 92.64 g (267.2 mmol, 97%)

$M_{cal.}$ (GDM-SA-Cl, $C_{15}H_{19}ClO_7$)=346.76 g/mol $^1$H-NMR (400.1 MHz, CDCl$_3$):

δ [ppm]=1.95 (s, 6H, C$\underline{H}_3$), 2.70-2.73 (t, 2H, C$\underline{H}_2$CH$_2$C(O)Cl, $^3J_{HH}$=6.9 Hz), 3.21-3.24 (t, 2H, CH$_2$C$\underline{H}_2$C(O)Cl, $^3J_{HH}$=6.8 Hz), 4.25-4.44 (m, 4H, OC$\underline{H}_2$CHORC H$_2$O), 5.34-5.46 (m, 1H, C$\underline{H}$), 5.60-5.63 (m, 2H, $\underline{H}_2$C=, cis), 6.13 (m, 2H, $\underline{H}_2$C=, trans).

$^{13}$C-NMR (100.6 MHz, CDCl$_3$):

δ [ppm]=18.25 ($\underline{C}H_3$), 29.32 ($\underline{C}H_2CH_2C(O)Cl$), 41.69 (CH$_2\underline{C}$H$_2$C(O)Cl), 62.38 (O$\underline{C}$H$_2$CHOR$\underline{C}$H$_2$O), 70.05 ($\underline{C}$H), 126.57 (H$_2\underline{C}$=), 135.58 (=$\underline{C}$(CH$_3$)C(O)OR), 166.77 (=C(CH$_3$)—$\underline{C}$(O)OR), 170.04 ($\underline{C}$(O)OR) and 172.81 ($\underline{C}$(O)Cl).

FT-IR: ṽ [cm$^{-1}$]=2961 and 2930 (m, ν(CH)), 1794 (vs, RCOCl ν C=O)), 1724 (vs, ν C=O)), 1638 (m, ν C=C)), 712 (m, ν C—Cl)).

μ-Raman: ṽ [cm$^{-1}$]=2965 u. 2932 (vs, ν C—H)), 1797 (w, RCOCl ν C=O)), 1722 (s, ν C=O)), 1639 (s, ν C=C)), 712 (w, ν C—Cl)), 439 (s, ν C—Cl)).

Synthesis of 4-{1,3-bis[(methacryloyl)oxy]propan-2-yloxy}-4-oxo-butanoic acid-triethylene glycol ester (GDM-SA-TEG)

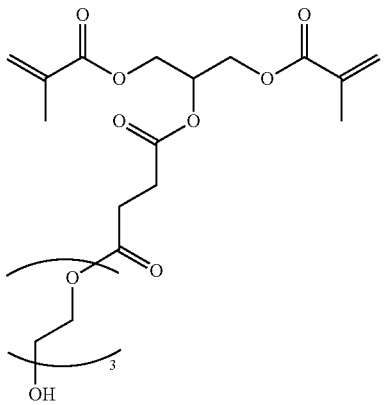

GDM-SA-TEG

The further reaction of GDM-SA to 4-{1,3-bis[(methacryloyl)oxy]propane-2-yloxy}-4-oxo-butanoic acid-triethyleneglycole ester (GDM-SA-TEG) was carried out analogous to the synthesis of MES-TEG: 48.88 g (325.5 mmol, 3.4 equiv.) TEG and 9.32 g (117.8 mmol, 1.2 equiv.) pyridine were dissolved in 100 ml dichloromethane under nitrogen atmosphere. 33.37 g (96.2 mmol, 1.0 equiv.) GDM-SA-Cl were added while cooling over ice and stirring. The mixture was stirred for 24 h at 30° C. and the product was then isolated, purified and stabilized as described before for MES-TEG.

The product is an alcohol with a branched hydrocarbon skeleton, carrying an organically polymerizable group (a methacrylate group) on both terminals of the skeleton opposite to the hydroxy groups.

Crude yield: 37.20 g

The crude yield does not account for the content of disubstituted alcohol (GDMSA$_2$TEG) formed in the reaction as a by-product. This content was determined as described above for MES-TEG with the aid of the $^1$H-NMR spectrum and is ≈20 Mol-%. Since the by-product is not disadvantageous in the further reaction, the mixture was not further purified.

If the content of GDMSA$_2$TEG is subtracted, the yield is 26.23 g (57.0 mmol, 59%).

M$_{cal.}$ (GDM-SA-TEG, C$_{21}$H$_{32}$O$_{11}$)=460.47 g/mol $^1$H-NMR (400.1 MHz, CDCl$_3$):

δ [ppm]=1.94 (s, 6H, C$\underline{H}_3$), 2.67 (s, 4H, CC$\underline{H}_2$C$\underline{H}_2$C), 3.60-3.62 (m, 2H, (OCH$_2$CH$_2$)$_2$OCH$_2$C$\underline{H}_2$OH), 3.65-3.74 (m, 8H, OC$\underline{H}_2$C$\underline{H}_2$OC$\underline{H}_2$OC$\underline{H}_2$CH$_2$OH), 4.25-4.45 (m, 6H, OC$\underline{H}_2$CHORC$\underline{H}_2$O and OC$\underline{H}_2$CH$_2$(OCH$_2$CH$_2$)$_2$OH), 5.36-5.43 (m, 1H, C$\underline{H}$), 5.61 (m, 2H, $\underline{H}_2$C=, cis), 6.12-6.13 (m, 2H, $\underline{H}_2$C=, trans).

$^{13}$C-NMR (100.6 MHz, CDCl$_3$):

δ [ppm]=18.26 ($\underline{C}$H$_3$), 28.89 and 29.02 (C$\underline{C}$H$_2$$\underline{C}$H$_2$C), 61.74, 62.47, 63.75, 69.03, 70.33, 70.57 and 72.47 (3× O $\underline{C}$H$_2$CH$_2$O and O$\underline{C}$H$_2$CHOR$\underline{C}$H$_2$O), 69.37 ($\underline{C}$H), 126.46 (H$_2\underline{C}$=), 135.64 (=$\underline{C}$(CH$_3$)C(O)OR), 166.78 (=C(CH$_3$)$\underline{C}$(O)OR), 171.40 and 172.06 (O$\underline{C}$(O)CH$_2$CH$_2\underline{C}$(O)O).

FT-IR: ṽ [cm$^{-1}$]=3473 (m, ν(OH)), 2957, 2929 and 2877 (m, ν CH)), 1725 (vs, ν C=O)), 1638 (m, ν C=C)).

μ-Raman: ṽ [cm$^{-1}$]=2962 and 2932 (vs, ν C—H)), 1722 (s, ν C=O)), 1639 (s, ν (C=C)).

Reaction of 4-[2-(methacryloyloxy)ethoxy]-4-oxo-butanoic acid-triethylene glycol ester (MES-TEG) with Silicon Tetraacetate and Hydrolysis/Condensation of the Product to Produce the Base Material Resin (GM-Resin)

10.37 g (39.2 mmol, 1.0 equiv.) silicon tetraacetate were admixed with 36.40 g 4-[2-(methacryloyloxy)ethoxy]-4-oxo-butanoic acid-triethylene glycol ester (MES-TEG) containing about 15 mol-% disubstituted by-product (MES$_2$TEG). This corresponds to a content of MES-TEG of 28.44 g (78.5 mmol, 2.0 equiv.). This mixture was first stirred for 1 min at room temperature and then heated for 3 h at 15 mbar to 50° C. Volatile products were removed from the product for 8 h in an oil pump vacuum and filtrated with the aid of compressed air using a filter having a pore size of 30 μm.

$^1$H-NMR (400.1 MHz, CDCl$_3$):

δ [ppm]=1.95 (s, 6H, C$\underline{H}_3$), 2.09-2.16 (m, Rest C$\underline{H}_3$COOSi), 2.67 (s, 8H, CC$\underline{H}_2$C$\underline{H}_2$C), 3.60-3.71 (m, 16H, OCH$_2$CHOCH$_2$CH$_2$OCH$_2$CH$_2$OSi), 3.92-4.09 (m, 4H, (OCH$_2$CH$_2$)$_2$O—CH$_2$C$\underline{H}_2$OSi), 4.24-4.25 (m, 4H, OC$\underline{H}_2$CH$_2$(OCH$_2$CH$_2$)$_2$OSi), 4.35 (m, 8H OC$\underline{H}_2$C$\underline{H}_2$O), 5.60-5.61 (m, 2H, $\underline{H}_2$C=, cis), 6.14 (m, 2H, $\underline{H}_2$C=, trans).

Then, the mixture was hydrolyzed in several steps at 30° C. To this end, 100 μl water were added thereto, stirred for 5 min, volatile components were removed in an oil pump vacuum for 5 h and it was continued to stir until the next interval. The hydrolysis degree of the Si—OAc groups and Si-OAlk groups was examined by $^1$H-NMR, respectively. The addition of water was repeated until the residual acetate content and the alcohol hydrolysis were as low as possible.

Crude yield: 33.96 g

The crude yield does not account for the content of disubstituted alcohol (MES$_2$TEG) contained in the MES-TEG but not converted in the synthesis. If this content is subtracted, the yield is 26.00 g (32.4 mmol, 83%).

M(GM)$_{cal.}$=≈802 g/mol $^1$H-NMR (400.1 MHz, CDCl$_3$):

δ [ppm]=1.95 (s, 6H, C$\underline{H}_3$), 2.08-2.11 (m, Rest C$\underline{H}_3$COOSi), 2.66 (s, 8H, CC$\underline{H}_2$C$\underline{H}_2$C), 3.58-3.71 (m, 16H, OCH$_2$C$\underline{H}_2$OC$\underline{H}_2$CH$_2$OC$\underline{H}_2$CH$_2$OSi), 3.92-4.02 (m, 4H, (OCH$_2$CH$_2$)$_2$OCH$_2$C$\underline{H}_2$OSi), 4.23-4.26 (m, 4H, OC$\underline{H}_2$CH$_2$(OCH$_2$CH$_2$)OSi), 4.35 (m, 8H, OC$\underline{H}_2$C$\underline{H}_2$O), 5.60 (m, 2H, $\underline{H}_2$C=, cis), 6.13 (m, 2H, $\underline{H}_2$C=, trans).

$^{29}$Si-NMR (75.5 MHz, acetone-d$^6$):

δ [ppm]=−82.76 (Q$^0$, ≈11%), −86.97 to −89.99 (Q$^1$, ≈35%), −94.00 to −96.99 (Q$^2$, ≈38%), −101.47 to −103.22 (Q$^3$, ≈16%).

If this diester (MES$_2$TEG) is separated before the production of the resin by chromatography, the resin is obtained with a yield up to 100%.

Reaction of 4-[2-(methacryloyloxy)ethoxy]-4-oxo-butanoic acid-hexaethylene glycolester (MES-HEG) with Silicon Tetraacetate and Hydrolysis/Condensation of the Product to Produce the Resin for Structural Variant I (SV I-Resin)

14.09 g (53.3 mmol, 1.0 equiv.) silicon tetraacetate were admixed with 56.82 g 4-[2-(Meth-acryloyloxy)ethoxy]-4-oxo-butanoic acid-hexaethylenglycol ester (MES-HEG) containing about 5 mol-% disubstituted by-product (content of MES-HEG: 52.76 g (106.7 mmol, 2.0 equiv.)) and reacted as described before in the synthesis of GM-Harz, volatile components were removed and filtrated under pressure.

$^1$H-NMR (400.1 MHz, CDCl$_3$):

δ [ppm]=1.95 (s, 6H, CH$_3$), 2.08-2.16 (m, Rest CH$_3$COOSi), 2.67 (s, 8H, CCH$_2$CH$_2$C), 3.57-3.71 (m, 40H, OCH$_2$CH$_2$(OCH$_2$CH$_2$)$_4$OCH$_2$CH$_2$OSi), 3.91-4.08 (m, 4H, (OCH$_2$CH$_2$)$_5$O—CH$_2$CH$_2$OSi), 4.23-4.26 (m, 4H, OCH$_2$CH$_2$(OCH$_2$CH$_2$)$_5$OSi), 4.35 (m, 8H OCH$_2$CH$_2$O), 5.60 (m, 2H, H$_2$C=, cis), 6.13 (m, 2H, H$_2$C=, trans).

The subsequent hydrolysis/condensation was carried out stepwise at 30° C. as described before in the synthesis of GM-Resin and was controlled using $^1$H-NMR.

Crude yield: 54.48 g

The crude yield does not account for the content of disubstituted alcohol (MES$_2$HEG) contained in the MES-HEG but not converted in the synthesis. If this content is subtracted, the yield is 50.42 g (47.0 mmol, 88%).

M(SV I)$_{cal.}$=≈1073 g/mol $^1$H-NMR (400.1 MHz, CDCl$_3$):

δ [ppm]=1.95 (s, 6H, CH$_3$), 2.06-2.11 (m, Rest CH$_3$COOSi), 2.67 (s, 8H, CCH$_2$CH$_2$C), 3.57-3.71 (m, 40H, OCH$_2$CH$_2$(OCH$_2$CH$_2$)$_4$OCH$_2$CH$_2$OSi), 3.91-4.01 (m, 4H, (OCH$_2$CH$_2$)$_5$O—CH$_2$CH$_2$OSi), 4.23-4.26 (m, 4H, OCH$_2$CH$_2$(OCH$_2$CH$_2$)$_5$OSi), 4.35 (m, 8H OCH$_2$CH$_2$O), 5.60-5.61 (m, 2H, H$_2$C=, cis), 6.13 (m, 2H, H$_2$C=, trans).

$^{29}$Si-NMR (75.5 MHz, acetone-d$^6$):

δ [ppm]=−82.79 and −83.47 (Q$^0$, 7%), −86.02 to −90.09 (Q$^1$, 30%), −93.63 to −97.40 (Q$^2$, 44%), −100.60 to −104.96 (Q$^3$, 19%).

If this diester (MES$_2$HEG) is separated chromatographically before the production of the resin, the resin is obtained in a yield of up to 100%.

Reaction of 4-{1,3-bis[(methacryloyl)oxy]propane-2-yloxy}-4-oxo-butanoic acid-triethylene glycol ester (GDM-SA-TEG) with Silicon Tetraacetate Und Hydrolysis/Condensation of the Product to Produce the Resin Structural Variant II (SV II-Resin)

The transesterification on silicon tetraacetate by GDM-SA-TEG was carried out as follows: 7.91 g (29.9 mmol, 1.0 equiv.) silicon tetraacetate was reacted with 40.13 g 4-{1,3-bis[(methacryloyl)oxy]propane-2-yloxy}-4-oxo-butanoic acid-triethylene glycol ester (GDM-SA-TEG) containing about 20 mol-% disubstituted by-product (GDM-SA-TEG content: 28.29 g (61.4 mmol, 2.0 equiv.)). Volatile components were then removed from the product and the product was filtrated under pressure.

$^1$H-NMR (400.1 MHz, CDCl$_3$):

δ [ppm]=1.94 (s, 12H, CH$_3$), 2.09-2.16 (m, residue CH$_3$COOSi), 2.66 (s, 8H, CCH$_2$CH$_2$C), 3.58-3.69 (m, 16H, OCH$_2$CH$_2$OCH$_2$CH$_2$CH$_2$OSi), 3.92-4.09 (m, 4H, (OCH$_2$CH$_2$)$_2$OCH$_2$CH$_2$OSi), 4.23-4.45 (m, 12H, OCH$_2$CHORCH$_2$O and OCH$_2$CH$_2$(OCH$_2$CH$_2$)$_2$OSi), 5.33-5.47 (m, 2H, CH), 5.61 (m, 4H, H$_2$C=, cis), 6.12 (m, 4H, H$_2$C=, trans).

The hydrolysis/condensation was carried out stepwise at 30° C. and was controlled using $^1$H-NMR, as described before in the synthesis of GM-Resin.

Crude yield: 32.01 g

The crude yield does not account for the content of disubstituted alcohol (GDMSA$_2$TEG) contained in the GDM-SA-TEG and which is not reacted in the synthesis. If this content is subtracted, the yield is 20.17 g (20.6 mmol, 69%).

M(SV II)$_{cal.}$=≈980 g/mol $^1$H-NMR (400.1 MHz, CDCl$_3$):

δ [ppm]=1.94 (s, 12H, CH$_3$), 2.07 (m, residue CH$_3$COOSi), 2.66 (s, 8H, CCH$_2$CH$_2$C), 3.58-3.75 (m, 16H, OCH$_2$CH$_2$OCH$_2$CH$_2$OCH$_2$CH$_2$OSi), 3.92-3.95 (m, 4H, (OCH$_2$CH$_2$)$_2$O—CH$_2$CH$_2$OSi), 4.23-4.45 (m, 12H, OCH$_2$CHOCH$_2$O and OCH$_2$CH$_2$(OCH$_2$CH$_2$)$_2$OSi), 5.37-5.46 (m, 2H, CH), 5.61 (m, 4H, H$_2$C=, cis), 6.12 (m, 4H, H$_2$C=, trans).

$^{29}$Si-NMR (75.5 MHz, acetone-d$^6$):

δ [ppm]=−82.80 (Q$^0$, ≈30%), −89.4 to −89.51 (Q$^1$, ≈38%), −96.51 to −96.78 (Q$^2$, ≈24%), −98.77 to −110.12 (Q$^3$, ≈8%).

Reaction of 4-[2-(methacryloyloxy)ethoxy]-4-oxo-butanoic acid-[3-hydroxy-2-hydroxymethylpropyl]-ester (MES-HPE) with Silicon Tetraacetate and Hydrolysis/Condensation of the Product to Produce the Resin for Structural Variant IV (SV IV-Resin)

The transesterification on silicon tetraacetate by MES-HPE was carried out as follows: 1.0 equivalent silicon tetraacetate was reacted with 2.0 equivalents of the mixture of monoester, diester and possibly triester. Volatile components were then removed from the product and the product was filtrated under pressure. The resulting product was not examined for the presence of unreacted triester; should it be contained, it contributes as a purely organic component to increase the cross-linking degree in the subsequent organic polymerization.

This is an example for the reaction of silanes (A) with alcohol blends (R$^{1'}$OH and R$^{2'}$(OH)$_2$). Parts of compounds which can be formed are exemplified below (these are parts of the structures (2) and (3) and the structure (9))

(9)

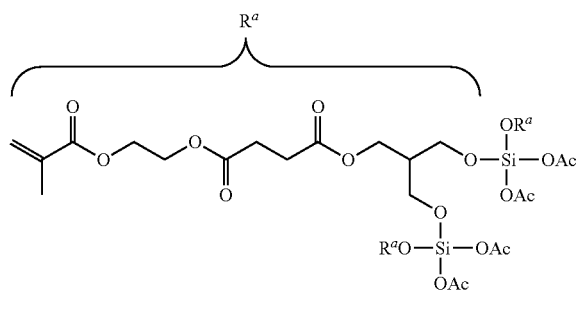

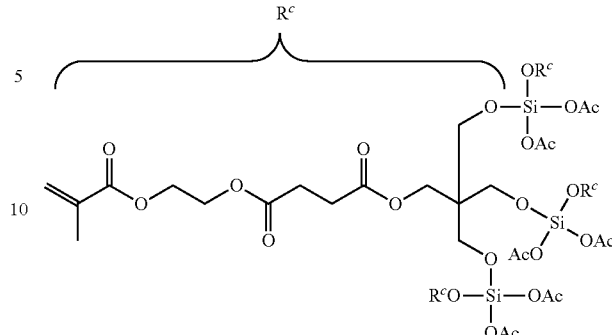

wherein it should be noted for compound (9) that the residue denoted as $R^a$ corresponds once to $R^2$ (bound to both Si atoms) and twice to $R^{2''}$(OH) (bound to a Si atom, respectively).

Reaction of 4-[2-(methacryloyloxy)ethoxy]-4-oxo-butanoic acid-glycerin ester MES-GE with Silicon Tetraacetate and Hydrolysis/Condensation of the Product to Produce the Resin for Structural Variant V (SV V-Resin)

Similar to the synthesis of GM-Resin, SV V-Resin is produced by reaction of MES-GE with silicon tetraacetate.

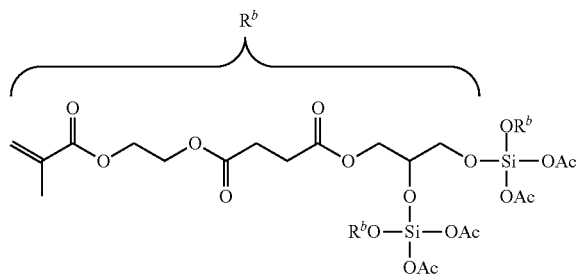

The displayed structure corresponds to structure (9); the statements made with respect to the SV IV-Resin correspondingly apply, wherein the residue $R^b$ replaces $R^a$.

Reaction of 4-[2-(methacryloyloxy)ethoxy]-4-oxo-butanoic acid-[3-hydroxy-2,2-dihydroxymethylpropyl]-ester MES-HDPE with Silicon Tetraacetate and Hydrolysis/Condensation of the Product to Produce the Resin for Structural Variant VI (SV VI-Resin)

Similar to the synthesis of GM-Resin, resin SV VI is produced by reaction of MES-HDPE with silicon tetraacetate. This is an example for the reaction of silanes (A) with alcohol blends ($R^{1'}$OH, $R^{2'}(OH)_2$ and $R^x(OH)_x$ with x=3). A network is formed in which, as mentioned above, a part of the organic residues can again carry free OH groups. A structural component in which the completely shown $R^c$ partly carries no OH groups, but the remaining residues $R^c$ can contain one or even two OH groups, is exemplified below.

Partial hydrolysis and condensation of ethyltriacetoxysilane (pHK-EtSi(OAc)$_3$)

5.00 g (21.4 mmol, 1.0 equiv.) ethyltriacetoxysilane were dissolved in 3.72 g (64.0 mmol, 3.0 equiv.) acetone-d$^6$ and admixed at 30° C. under stirring with 285 μl (15.8 mmol, 0.7 equiv.) water in form of a $10^{-2}$ molar hydrochloric acid solution (pHK-EtSi(OAc)$_3$-V1). The blend was stirred for 24 h at room temperature and not further refined in order to not affect the equilibrium.

The synthesis was analogously carried out with a 10-01 and a 1 molar hydrochloric acid solution (pHK-EtSi(OAc)$_3$-V2 and pHK-EtSi(OAc)$_3$-V3). The evaluation of the corresponding $^1$H-NMR spectra for pHK-EtSi(OAc)$_3$-V1 to pHK-EtSi(OAc)$_3$-V3 is summarized in the following table A5.

TABLE A5

Integrals of the CH$_3$ groups in the $^1$H-NMR spectra of the mixtures pHK-EtSi(OAc)$_3$-V1 to pHK-EtSi(OAc)$_3$-V3 for the partial hydrolysis and condensation of ethyltriacetoxysilane in acetone-d$^6$ after 24 h.

| Mixture | c(HCl) [mol/l] | Content of C$\underline{H}_3$COOSi 2.06-2.10 ppm [%] | Content of C$\underline{H}_3$COOH 2.01 ppm [%] |
|---|---|---|---|
| pHK-EtSi(OAc)$_3$-V1 | $10^{-2}$ | 51 | 49 |
| pHK-EtSi(OAc)$_3$-V2 | $10^{-1}$ | 51 | 49 |
| pHK-EtSi(OAc)$_3$-V3 | 1 | 54 | 46 |

The results of the $^{29}$Si-NMR measurements for pHK-EtSi(OAc)$_3$-V1 to pHK-EtSi(OAc)$_3$-V3 for the determination of the condensation degree of the mixtures are summarized in table A6. The condensation degree was determined according to the following formula.

$$K = \frac{1M^1 + 1D^1 + 2D^2 + 1T^1 + 2T^2 + 3T^3 + 1Q^1 + 2Q^2 + 3Q^3 + 4Q^4}{1(M^0 + M^1) + 2(D^0 + D^1 + D^2) + 3(T^0 + T^1 + T^2 + T^3) + 4(Q^0 + Q^1 + Q^2 + Q^3 + Q^4)}$$

For the partial hydrolysis and condensation of ethyltriacetoxysilane, only T groups have to be considered.

TABLE A6

Distribution of the T groups in the $^{29}$Si-NMR spectra of the mixtures pHK-EtSi(OAc)$_3$-V1 to pHK-EtSi(OAc)$_3$-V3 for the partial hydrolysis of ethyltriacetoxysilane after 6 h.

| Mixture | c(HCl) [mol/l] | $T^0$ content −43.91 ppm [%] | $T^1$ content −49.12 to −52.82 ppm [%] | $T^2$ content −55.99 to −60.47 ppm [%] | $T^3$ content −66.04 to −67.20 ppm [%] | K [%] |
|---|---|---|---|---|---|---|
| pHK-EtSi(OAc)$_3$-V1 | $10^{-2}$ | <1 | 69 | 15 | 16 | 49 |
| pHK-EtSi(OAc)$_3$-V2 | $10^{-1}$ | 2 | 66 | 16 | 16 | 49 |
| pHK-EtSi(OAc)$_3$-V3 | 1 | 7 | 59 | 18 | 16 | 48 |

Co-Condensation of the Product of 4-[2-(methacryloyloxy)ethoxy]-4-oxo-butanoic acid-triethylene glycol ester and silicon tetraacetate ((MES-TEG)$_2$-Si(OAc)$_2$) with Partially Hydrolyzed ethyltriacetoxysilane (pHK-EtSi(OAc)$_3$-V3) to Produce the Resin for Structural Variant III (SV III-Resin)

In a further synthesis, the addition product of MES-TEG and silicon tetraacetate ((MES-TEG)$_2$Si(OAc)$_2$) was reacted with partially condensed ethyltriacetoxysilane (pHK-EtSi (OAc)$_3$-V3).

To this end, 9.56 g (36.2 mmol, 1.0 equiv.) were admixed with 33.55 g (85.1 mmol) 4-[2-(methacryloyloxy)ethoxy]-4-oxo-butanoic acid-triethylene glycol ester containing about 15 mol-% disubstituted by-product, as mentioned above (MES-TEG content: 26.21 g (72.3 mmol, 2.0 equiv.), reacted, and volatile components were removed from the reaction product. Further, 8.49 g (36.2 mmol, 1.0 equiv.) ethyltriacetoxysilane were dissolved in 6.32 g (108.8 mmol, 3.0 equiv.) acetone, 480 µl water (26.6 mmol, 0.74 equiv.) in the form of a $10^{-2}$ molar hydrochloric acid solution were added, and it was stirred for 24 h at 30° C. Then, both mixtures were combined and the solvent was removed under reduced pressure or in an oil pump vacuum.

$^1$H-NMR (400.1 MHz, CDCl$_3$):

δ [ppm]=0.71-1.05 (m, 5H, C$\underline{H}_3$C$\underline{H}_2$Si), 1.95 (s, 6H, C$\underline{H}_3$), 2.08-2.16 (m, residue C$\underline{H}_3$COOSi), 2.67 (s, 8H, CC$\underline{H}_2$C$\underline{H}_2$C), 3.58-3.71 (m, 16H, OCH$_2$C$\underline{H}_2$OC$\underline{H}_2$CH$_2$O—C$\underline{H}_2$CH$_2$OSi), 3.92-4.09 (m, 4H, (OC$\underline{H}_2$CH$_2$)$_2$OCH$_2$C$\underline{H}_2$OSi), 4.23-4.27 (m, 4H, OC$\underline{H}_2$CH$_2$(OCH$_2$CH$_2$)$_2$OSi), 4.35 (m, 8H OC$\underline{H}_2$C$\underline{H}_2$O), 5.60-5.61 (m, 2H, $\underline{H}_2$C=, cis), 6.13 (m, 2H, $\underline{H}_2$C=, trans).

Both compounds were then stepwise hydrolyzed at 30° C. as described in more detail for the synthesis of GM-Resin and co-condensed. The reaction was controlled by $^1$H-NMR.

$^1$H-NMR (400.1 MHz, CDCl$_3$):

δ [ppm]=0.64-1.00 (m, 5H, C$\underline{H}_3$C$\underline{H}_2$Si), 1.95 (s, 6H, C$\underline{H}_3$), 2.06-2.08 (m, residue C$\underline{H}_3$COOSi), 2.66 (s, 8H, CC$\underline{H}_2$C$\underline{H}_2$C), 3.59-3.72 (m, 16H, OCH$_2$C$\underline{H}_2$OC$\underline{H}_2$CH$_2$O—C$\underline{H}_2$CH$_2$OSi), 3.92-3.95 (m, 4H, (OC$\underline{H}_2$CH$_2$)$_2$OCH$_2$C$\underline{H}_2$OSi), 4.23-4.26 (m, 4H, OC$\underline{H}_2$CH$_2$(OCH$_2$CH$_2$)$_2$OSi), 4.35 (m, 8H OC$\underline{H}_2$C$\underline{H}_2$O), 5.60 (m, 2H, $\underline{H}_2$C=, cis), 6.13 (m, 2H, $\underline{H}_2$C=, trans).

$^{29}$Si-NMR (75.5 MHz, acetone-d$^6$):

δ [ppm]=−50.12 to −61.44 ($T^1$, ≈20%), −58.06 to −61.44 ($T^2$, ≈28%), −66.87 to −67.26 ($T^3$, ≈5%), −82.81 ($Q^0$, ≈3%), −86.10 to −89.42 ($Q^1$, ≈9%), −93.70 to −96.25 ($Q^2$, ≈22%), −100.74 to −103.34 ($Q^3$, ≈12%), −109.67 ($Q^4$, <1%).

Crude yield: 33.21 g

The crude yield does not account for the content of disubstituted alcohol (MES$_2$TEG) contained in MES-TEG, but not reacted in the synthesis. If this content is subtracted, the yield is 25.87 g (60.2 mmol, 83%).

If the diester (MES$_2$TEG) is chromatographically separated before the production, the resin is obtained in a yield of up to 100%.

M(SV III)$_{cal.}$=≈860 g/mol

Polymerization Products

To the resin systems to be analyzed, 1 wt.-% of the photoinitiator Lucirin-TPO was respectively added, and it was stirred at 30° C. or 40° C. until the initiator was dissolved (about 24-48 h).

Corresponding to DIN 53504, test pieces having a total length of 54 mm and a cross section of 2 mm×4 mm were produced. The ends were irradiated for 30 s and the web/bar was irradiated for 100 s per side with a blue light lamp of the company VOCO in the wavelength range of 380-520 nm.

Besides the above-mentioned resin systems, the photopolymerization product of GM-Resin with Lucirin and trimethylolpropane-tri(3-mercaptopropionate) (TMPMP) was also examined. To this end, 0.54 g (1.3 mmol) TMPMP was dissolved in a mixture of 1.98 g (2.5 mmol) GM-Resin and 0.02 mg Lucirin. The obtained resin blend was cured by photo-induction in a test piece form (diameter about 10 mm, thickness about 2 mm).

The measurements of tensile strengths showed that the addition of a trithiol compound provided a more flexible product compared with the same resin without addition of thiol. This is probably because the cross-linking becomes more widely spaced due to the thiol compound.

For the examinations of degradation and biocompatibility tests, test pieces having a disk shape (diameter about 10 mm, height about 2 mm) and a weight of about 200 mg were produced by irradiation of the resin system with the aforementioned light source. Each side of the disk was irradiated for 100 s, and the rim for further 30 s. The individual test pieces were then weighed and stored individually in sample vials with 1 ml buffer solution. After 3 days the buffer solutions were exchanged. After 1 week, 4 weeks and 16 weeks (with a weekly renewal of the buffer solutions), test pieces were withdrawn and dried. Then, their weight loss was measured.

Alternatively, 1 wt.-% of a thermal initiator such as dibenzoyl peroxide can be added to the resin systems and stirred at 40° C. until dissolved (about 24 h). Then, samples can be produced by curing the formulation at 100° C. for 4 h.

The invention claimed is:

1. A silane or silane blend, obtainable by reaction of a hydrolyzable silane represented by the formula (A)

$$SiR_4 \qquad (A),$$

wherein R is a hydrolytically condensable group or hydroxy,
with a compound $R^*(OH)_x$,
wherein x is 1, 2, 3 or larger than 3, $R^*$ is a straight-chain or branched hydrocarbon skeleton which is monovalent, divalent, trivalent or multivalent, depending on the number of x, and which has a hydrocarbon-containing chain interrupted by at least two —C(O)O— groups,
wherein in the individual hydrocarbon units formed by interruptions, up to 8 carbon atoms succeed each other, and the end or, in case of branched structures, at least one end of the hydrocarbon-containing chain remote from the only hydroxyl group or of one of the hydroxyl groups, carries an organically polymerizable group, wherein the compound $R^*(OH)_x$ is otherwise unsubstituted or comprises further substituents, and
wherein each of the OH groups of the compound $R^*(OH)_x$ is an alcohol group or a part of a carboxylic acid group, wherein compounds $R^*(OH)_x$ with x>1 can contain alcohol groups and carboxylic acid groups or can be polyalcohols or polycarboxylic acids.

2. The silane or silane blend according to claim 1, wherein R represents R'COO⁻ or OR' or OH, wherein R' is a straight-chain, branched or a non-aromatic ring-containing alkyl.

3. The silane or silane blend according to claim 2, wherein R' is methyl or ethyl.

4. The silane or silane blend according to claim 1, wherein the hydrocarbon chain of the residue $R^*$ is further interrupted by oxygen atoms and/or sulfur atoms.

5. The silane or silane blend according to claim 1, wherein in the individual hydrocarbon units formed by interruptions within the hydrocarbon-containing chain which is interrupted by two to six —C(O)O— groups, and not more than four carbon atoms succeed each other.

6. The silane or silane blend according to claim 1, wherein the hydrocarbon-containing chain of the residue $R^*$ is interrupted by at least three —C(O)— groups.

7. The silane or silane blend according to claim 1, wherein the organically polymerizable group comprises at least one organically polymerizable C=C double bond or an epoxide ring.

8. The silane or silane blend according to claim 7, wherein the polymerizable C=C double bond is part of an acrylate group or methacrylate group.

9. The silane or silane blend according to claim 1, wherein the hydrocarbon chain of the residue $R^*$ comprises alkylene units which are optionally substituted with one or more groups selected from among hydroxyl groups, carboxylic acid groups, phosphate groups, phosphonic acid groups, phosphoric acid groups, amino groups and amino acid groups.

10. The silane or silane blend according to claim 1, wherein the residue $R^*$ is a straight chain or a branched chain.

11. The silane or silane blend according to claim 1, wherein the hydrolytically condensable group R is selected from among acyl, alkyl and alkoxy.

12. A process for the production of a silane or a silane blend according to claim 1, wherein a silane having the formula (A) as defined in claim 1 is reacted with a compound $R^*6(OH)_x$ as defined in claim 1.

13. The process according to claim 12, wherein the silane and the compound $R^*(OH)_x$ are in a molar ratio of between 1:1.5 to 1:2.5.

* * * * *

UNITED STATES PATENT AND TRADEMARK OFFICE
CERTIFICATE OF CORRECTION

PATENT NO. : 10,259,829 B2
APPLICATION NO. : 15/509373
DATED : April 16, 2019
INVENTOR(S) : Herbert Wolter et al.

It is certified that error appears in the above-identified patent and that said Letters Patent is hereby corrected as shown below:

In the Specification

Column 18, Lines 45 and 46: "=5mol-%" should read --≈5mol%--.
Column 23, Line 52: "Und Hydrolysis/Condensation" should read --and hydrolysis/condensation--.
Column 26, Line 31: "10-01" should read --$10^{-1}$--.

Signed and Sealed this
Sixth Day of October, 2020

Andrei Iancu
*Director of the United States Patent and Trademark Office*